US009593065B2

(12) United States Patent
Schulz et al.

(10) Patent No.: US 9,593,065 B2
(45) Date of Patent: Mar. 14, 2017

(54) PROCESS FOR PREPARING ACRYLIC ACID FROM METHANOL AND ACETIC ACID

(71) Applicant: BASF SE, Ludwigshafen (DE)

(72) Inventors: Lukas Schulz, Mannheim (DE);
Nicolai Tonio Woerz, Friedelsheim (DE); Tim Blaschke, Stuttgart (DE); Marco Hartmann, Woerth (DE); Frank Huetten, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/794,955

(22) Filed: Jul. 9, 2015

(65) Prior Publication Data

US 2016/0031789 A1   Feb. 4, 2016

Related U.S. Application Data

(60) Provisional application No. 62/031,171, filed on Jul. 31, 2014.

(30) Foreign Application Priority Data

Jul. 31, 2014   (DE) .................. 10 2014 011 476

(51) Int. Cl.
| | | |
|---|---|---|
| *C07C 51/347* | (2006.01) | |
| *B01J 23/50* | (2006.01) | |
| *B01J 27/198* | (2006.01) | |
| *C07C 57/04* | (2006.01) | |
| *C07C 45/38* | (2006.01) | |
| *C07C 51/353* | (2006.01) | |
| *C07C 45/32* | (2006.01) | |
| *C07C 45/78* | (2006.01) | |

(52) U.S. Cl.
CPC ............ *C07C 51/347* (2013.01); *B01J 23/50* (2013.01); *B01J 27/198* (2013.01); *C07C 45/32* (2013.01); *C07C 45/38* (2013.01); *C07C 45/783* (2013.01); *C07C 51/353* (2013.01); *C07C 57/04* (2013.01)

(58) Field of Classification Search
None
See application file for complete search history.

(56) References Cited

U.S. PATENT DOCUMENTS

| | | | |
|---|---|---|---|
| 4,348,540 A * | 9/1982 | Ferris ................. | B01D 3/143 203/42 |
| 2012/0071688 A1 | 3/2012 | Herzog et al. | |
| 2013/0085294 A1 | 4/2013 | Peterson et al. | |
| 2014/0128636 A1 | 5/2014 | Peterson et al. | |

FOREIGN PATENT DOCUMENTS

WO   WO 2012/034929 A2   3/2012

OTHER PUBLICATIONS

International Search Report and Written Opinion issued Sep. 15, 2015 in PCT/EP2015/065689 (with English Translation od Category of Cited Documents).

* cited by examiner

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

A process for preparing acrylic acid from methanol and acetic acid, comprising (i) contacting a gaseous stream S0 comprising methanol, oxygen and inert gas with an oxidation catalyst to obtain a gaseous stream S1 comprising formaldehyde and inert gas; (ii) removing at least a portion of the inert gas present in S1 from at least a portion of the formaldehyde present in S1 by absorbing this formaldehyde in an absorbent to obtain a gaseous stream S2 comprising the portion of the inert gas removed, and to obtain a stream S3 comprising absorbent and absorbate comprising formaldehyde; (iii) optionally removing a portion or the entirety of the absorbent present in stream S3, such that a stream S3*a* remains from stream S3, and producing a stream S4 from at least stream S3 or stream S3*a* and a stream S5 comprising acetic acid; and (iv) contacting stream S4 in gaseous form with an aldol condensation catalyst to obtain a gaseous stream S6 comprising acrylic acid.

25 Claims, 1 Drawing Sheet

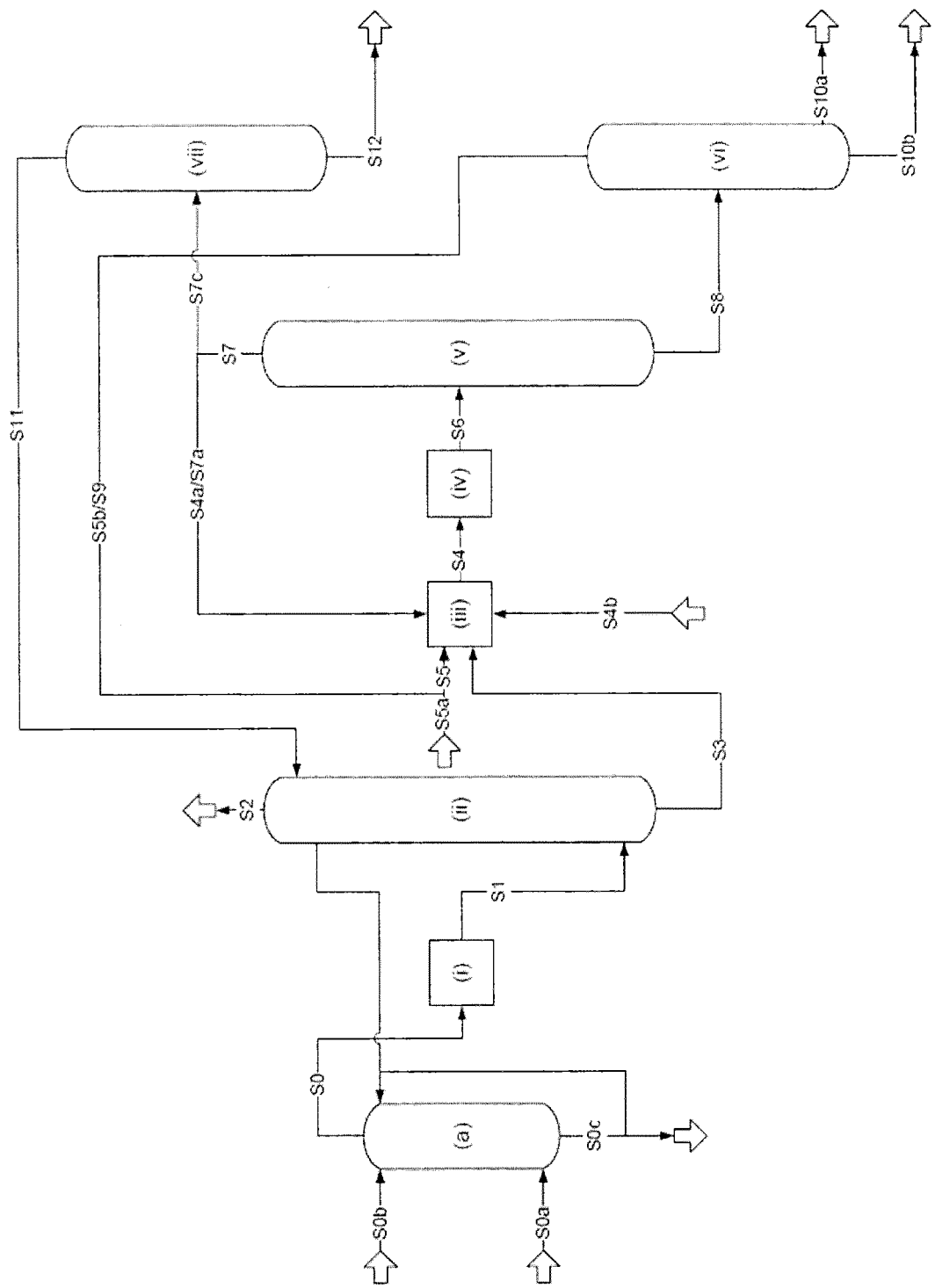

PROCESS FOR PREPARING ACRYLIC ACID FROM METHANOL AND ACETIC ACID

The present invention relates to a process for preparing acrylic acid from methanol and acetic acid, in which methanol is converted by oxidation to formaldehyde and the latter is reacted with acetic acid over an aldol condensation catalyst to give acrylic acid.

Acrylic acid, an important monomer for production of homo- and copolymers, is typically obtained by a heterogeneously catalyzed two-stage partial oxidation proceeding from propene, with acrolein as intermediate.

A possible alternative is the preparation of acrylic acid in a heterogeneously catalyzed gas phase reaction by a condensation of formaldehyde and acetic acid. To date, no satisfactorily high conversions based on formaldehyde have been attained with known catalyst systems in a single reactor pass and under reaction conditions which lead to a selectivity of acrylic acid formation based on formaldehyde conversion of more than 90%, and so no economically viable process was possible.

For example, US 2013/0085294 A1 discloses a process for preparing acrylic acid from acetic acid and formaldehyde as alkylating agent. The catalysts used comprise titanium and vanadium, and optionally oxidic additives such as $SiO_2$, $Al_2O_3$ and $ZrO_2$. In the distillative workup, the product stream is separated into an acrylic acid-rich stream and a formaldehyde-rich stream, using a water-immiscible solvent. The acrylic acid-rich stream is separated by azeotropic distillation into a crude acrylic acid stream and an acetic acid stream. The acetic acid stream is recycled upstream of the condensation reactor. The formaldehyde-rich stream from the first separation stage is separated in a further distillation column into a formaldehyde stream and a stream comprising acetic acid and water. The formaldehyde stream is recycled upstream of the reactor. The stream comprising acetic acid and water is separated in a liquid-liquid extraction or by azeotropic distillation into an acetic acid stream and a water stream. This acetic acid stream too is recycled into the condensation reaction.

The formaldehyde used in the preparation of acrylic acid from acetic acid and formaldehyde is preferably obtained by partial oxidation of methanol. In the course of this partial oxidation, inert dilute gases are always employed. However, these lead to dilution of the reaction mixture in the acrylic acid preparation stage and hence to a reduction in the efficiency of the process.

One of the objects underlying the present invention was therefore that of providing a novel process, especially one that can be performed advantageously on the industrial scale, for preparing acrylic acid by aldol condensation of formaldehyde and acetic acid, in which the formaldehyde used is obtained by partial oxidation of methanol.

It has been found that, surprisingly, such a process can be implemented by sending the stream which comprises formaldehyde and inert gas and has been obtained by partial oxidation of methanol to an absorption stage specifically tailored to the process before it is used as a reactant stream in the acrylic acid preparation. This enables, in the subsequent stage of acrylic acid preparation, with the same total catalyst hourly space velocity, an increase in the catalyst hourly space velocity of reactants and hence in the overall efficiency of the process.

The present invention therefore relates to a process for preparing acrylic acid from methanol and acetic acid, comprising (i) contacting a gaseous stream S0 comprising methanol, oxygen and inert gas with an oxidation catalyst to obtain a gaseous stream S1 comprising formaldehyde and inert gas;

(ii) removing at least a portion of the inert gas present in S1 from at least a portion of the formaldehyde present in S1 by absorbing this formaldehyde in an absorbent to obtain a gaseous stream S2 comprising the portion of the inert gas removed, and to obtain a stream S3 comprising absorbent and absorbate comprising formaldehyde;

(iii) optionally removing a portion or the entirety of the absorbent present in stream S3, such that a stream S3a remains from stream S3, and producing a stream S4 from at least stream S3 or stream S3a and a stream S5 comprising acetic acid; and (iv) contacting stream S4 in gaseous form with an aldol condensation catalyst to obtain a gaseous stream S6 comprising acrylic acid.

It has further been found that this process in (ii), together with the inert gas removal, enables the removal of methanol unconverted in the partial oxidation, which allows another increase in the catalyst hourly space velocity of reactants in the acrylic acid preparation stage which follows the absorption stage, and hence in the overall efficiency of the process, particularly with regard to the space-time yield.

Contacting in (i)

In stage (i) of the process according to the invention, stream S0 comprising methanol, oxygen and inert gas is contacted with an oxidation catalyst to obtain a stream S1 comprising formaldehyde and inert gas.

In principle, stream S0 is not subject to any particular restrictions in terms of its content of methanol, oxygen and inert gas. Preferably from 30% to 100% by weight, further preferably from 50% to 98% by weight, further preferably from 70% to 95% by weight, further preferably from 75% to 90% by weight, further preferably from 77% to 85% by weight, of stream S0 consists of methanol, oxygen and inert gas.

The weight ratio of inert gas to oxygen in stream S0 may, for example, be in the range from 1:1 to 10:1. Preferably, in stream S0, the weight ratio of inert gas to oxygen is in the range from 2:1 to 6:1, further preferably in the range from 2.5:1 to 4:1, further preferably in the range from 3:1 to 3.5:1.

The weight ratio of inert gas to methanol in stream S0 may, for example, be in the range from 1:1 to 10:1. Preferably, in stream S0, the weight ratio of methanol to oxygen is in the range from 1.5:1 to 6:1, further preferably in the range from 2:1 to 3.5:1, further preferably in the range from 2.5:1 to 3:1.

Preferably, in stream S0, the weight ratio of inert gas to oxygen is in the range from 2.5:1 to 4:1, further preferably in the range from 3:1 to 3.5:1, and at the same time, in each of the two aforementioned cases, the weight ratio of methanol to oxygen is in the range from 2:1 to 3.5:1 or preferably in the range from 2.5:1 to 3:1.

In this document, inert gas shall be all the materials that are gaseous under the process conditions selected in each case and are inert in both stages (i) and (iv). "Inert" in this context means that the gaseous material in a single pass through the particular reaction stage is converted to an extent of less than 5 mol %, preferably to an extent of less than 2 mol %, more preferably to an extent of less than 1 mol %. Regardless of this definition, water, carbon monoxide, carbon dioxide, hydrogen, methylene glycol, hemiformal, acetaldehyde, methyl acrylate, methyl acetate, ethene, acetone and methyl formate shall not be covered by the term "inert gas". In this context, the term "inert gas" as used in the context of present invention refers either to a single gas or to a mixture of two or more gases. For example, useful inert gases include helium, neon, argon, krypton, radon, xenon, nitrogen, sulfur hexafluoride and gas mixtures of two or more thereof. Preferably, the inert gas in (i) comprises nitrogen, there being no restrictions in principle with regard to the proportion of nitrogen. If the inert gas in (i) comprises nitrogen, preferably at least 95% by weight, further preferably at least 97% by weight, further preferably at least 98% by weight, of the inert gas consists of nitrogen.

It is conceivable in principle that stream S0 consists of methanol, oxygen and inert gas. Preferably, stream S0 comprises at least one further component in addition to methanol, oxygen and inert gas, stream S0 further preferably additionally comprising water, or formaldehyde, or water and formaldehyde. Further preferably, stream S0, in addition to methanol, oxygen and inert gas, also comprises water and formaldehyde.

Preferably from 1% to 30% by weight, further preferably from 10% to 25% by weight, further preferably from 15% to 25% by weight, of stream S0 consists of the at least one further component in addition to methanol, oxygen and inert gas. Preferably from 1% to 30% by weight, further preferably from 10% to 25% by weight, further preferably from 15% to 25% by weight, of stream S0 consists of water or of formaldehyde or of water and formaldehyde. Further preferably from 1% to 30% by weight, further preferably from 10% to 25% by weight, further preferably from 15% to 25% by weight, of stream S0 consists of water and formaldehyde.

The weight ratio of water to oxygen in stream S0 is, for example, in the range from 0.1:1 to 5:1. Preferably, in stream S0, the weight ratio of water to oxygen is in the range from 0.5:1 to 2:1, further preferably in the range from 1:1 to 1.5:1.

The weight ratio of formaldehyde to oxygen in stream S0 may be in the range from 0.01:1 to 5:1. Preferably, in stream S0, the weight ratio of formaldehyde to oxygen is in the range from 0.1:1 to 1:1, further preferably in the range from 0.25:1 to 0.75:1.

Preferably, in stream S0, the weight ratio of water to oxygen is in the range from 0.5:1 to 2:1, further preferably in the range from 1:1 to 1.5:1, and at the same time, in each of the two aforementioned cases, the weight ratio of formaldehyde to oxygen is in the range from 0.1:1 to 1:1 or preferably in the range from 0.25:1 to 0.75:1.

In principle, there are no particular restrictions with regard to the nature of the oxidation catalyst in (i), provided that the contacting of the oxidation catalyst with stream S0 can give a stream S1 comprising formaldehyde and inert gas, and hence a partial oxidation of methanol is effected. Consequently, useful oxidation catalysts here are those comprising noble metals, for example copper, silver or gold, in the form of an unsupported catalyst or supported on a support material, and also iron catalysts, especially iron-molybdenum catalysts. Preferably, the oxidation catalyst in (i) comprises silver, where the latter may be in elemental form or in the form of a suitable compound, for example in the form of silver(I) oxide, mixed silver oxide, silver halide, silver sulfide, silver nitrate, silver sulfate or in the form of a mixture of two or more thereof. Preferably, the silver is in elemental form in the oxidation catalyst in (i). The oxidation catalyst comprising elemental silver in (i) may be used in the form of an unsupported catalyst or a supported catalyst, it being preferable that the oxidation catalyst in (i) is an unsupported catalyst. Preferably, the oxidation catalyst in (i) which comprises elemental silver and is in the form of an unsupported catalyst comprises from 50% to 100% by weight, further preferably from 80% to 100% by weight, further preferably from 90% to 100% by weight, further preferably from 95% to 100% by weight, further preferably from 99% to 100% by weight, further preferably from 99.5% to 100% by weight, further preferably from 99.99% to 100% by weight, of silver, calculated in each case as elemental silver and based on the total weight of the unsupported catalyst.

The silver-comprising oxidation catalyst in (i) may be in the form of granules, of a knit or of a mixture thereof for example. Preferably, the oxidation catalyst in (i) is in the form of granules, the granules not being subject to any particular restrictions in principle with regard to the particle size. Preferably, the granules have a particle size distribution, determined by means of DIN ISO 3310 from 2010, in the range from 0.1 to 5 mm, further preferably from 0.2 to 4 mm, further preferably from 0.3 to 3 mm, further preferably from 0.5 to 2 mm.

The contacting of stream S0 with an oxidation catalyst in (i) to obtain a stream S1 comprising formaldehyde and inert gas is preferably effected in at least one reactor, further preferably in at least two reactors, for example in two, three, four or five reactors, where at least two reactors may be arranged in parallel or at least two reactors in series or at least two reactors in parallel and at least two reactors in series.

It is likewise possible that at least two, preferably two, three, four or five, further preferably two, three or four, further preferably two or three, further preferably two, reactors connected in parallel are operated in alternation, with at least one reactor always in operation in this alternating mode of operation. Preferably, the contacting in (i) is effected in at least one reactor, preferably at least two reactors, further preferably in at least two reactors connected in parallel, which are further preferably operated in alternation. Preferably, these reactors are configured as fixed bed reactors, for example as shell and tube reactors or thermoplate reactors. In the case of a shell and tube reactor, the catalytically active fixed bed is advantageously within the catalyst tubes, with fluid heat carrier flowing around them.

The catalyst hourly space velocity with regard to the contacting in (i) in the reactor is preferably chosen such that a balanced ratio of the parameters of conversion, selectivity, space-time yield, reactor geometry and reactor dimensions can be achieved, the catalyst hourly space velocity with regard to the contacting in (i) in the reactor being defined as mass of S0 in kg per hour and per unit mass of catalyst in kg. Preferably, the contacting in (i) in the reactor is effected at a catalyst hourly space velocity in the range from 5 to 100 kg/(h*kg), further preferably in the range from 15 to 80 kg/(h*kg), further preferably in the range from 25 to 60 kg/(h*kg).

The contacting in (i) in the reactor is not subject to any particular restrictions with regard to the temperature of the catalyst bed, provided that the contacting of the oxidation catalyst with stream S0 gives a stream S1 comprising formaldehyde and inert gas. Preferably, the contacting in (i) in the reactor is effected at a temperature of the catalyst bed in the range from 500 to 900° C., further preferably in the range from 600 to 800° C., further preferably in the range from 650 to 750° C.

The contacting in (i) in the reactor is not subject to any particular restriction with regard to the pressure in the reactor, provided that the contacting of the oxidation catalyst with stream S0 gives a stream S1 comprising formaldehyde and inert gas. Preferably, the contacting in (i) in the reactor is effected at a pressure in the range from 0.5 to 2.5 bar, further preferably in the range from 0.8 to 2.2 bar, further preferably in the range from 1 to 2 bar.

All pressure figures in the context of the present invention relate to absolute pressures.

Preferably, the contacting in (i) in the reactor is effected at a temperature of the catalyst bed in the range from 500 to 900° C., further preferably in the range from 600 to 800° C., further preferably in the range from 650 to 750° C., and at the same time, for each of the aforementioned temperature ranges, a pressure in the range from 0.5 to 2.5 bar, preferably in the range from 0.8 to 2.2 bar, further preferably in the range from 1 to 2 bar.

The stream S1 comprising formaldehyde and inert gas obtained in (i) consists preferably of 55% to 80% by weight, further preferably of 60% to 75% by weight, further preferably of 65% to 70% by weight, of formaldehyde and inert gas, based in each case on the total weight of the stream.

It is conceivable in principle that stream S1 consists of formaldehyde and inert gas. Preferably, stream S1 comprises at least one further component. Further preferably, stream S1 additionally comprises water, or oxygen, or water and oxygen. Further preferably, stream S1 comprises, in addition to formaldehyde and inert gas, water and oxygen. Preferably from 15% to 40% by weight, further preferably from 20% to 35% by weight, further preferably from 25% to 30% by weight, of stream S1 consists of water and oxygen.

Preferably, the weight ratio of water to oxygen in stream S1 is in the range from 25:1 to 50:1, further preferably in the range from 35:1 to 45:1.

Preferably 15% to 40% by weight, further preferably from 20% to 35% by weight, further preferably from 25% to 30% by weight, of the stream S1 additionally comprising water and oxygen consists of water and oxygen, and at the same time, for each of the aforementioned cases, the weight ratio of water to oxygen is preferably in the range from 25:1 to 50:1, further preferably in the range from 35:1 to 45:1.

It is further possible that stream S1 comprises at least one further component in addition to formaldehyde and inert gas and preferably water and oxygen. For example, stream S1 may additionally comprise at least one compound selected from the group consisting of methanol, hydrogen, carbon dioxide, carbon monoxide, methylene glycol and hemiformal. Preferably, the total content of these compounds in stream S1 is in the range from 1% to 10% by weight, further preferably in the range from 3% to 9% by weight, further preferably in the range from 5% to 8% by weight.

Preferably, the process according to the present invention additionally comprises (a) contacting, preferably in countercurrent, a stream S0a comprising oxygen, inert gas and preferably water with a stream S0b comprising methanol to obtain a stream S0c depleted of inert gas and a stream S0 enriched in inert gas.

In this case, step (a) can be conducted in any suitable apparatus or any suitable combination of apparatuses, it being preferable to conduct step (a) preferably in a column equipped with separating internals, preferably ones which increase the surface area, preferably with random packings. In this case, stream S0b is conducted into the column at the top in liquid form; stream S0a is conducted into the column from the bottom in gaseous form. Stream S0 leaves the column at the upper end thereof, preferably in methanol-saturated form. A column operated in such a way is also referred to as saturation column.

Preferably at least 80% by weight, further preferably at least 90% by weight, further preferably at least 95% by weight, further preferably at least 98% by weight, further preferably at least 99% by weight, of stream S0a consists of oxygen, inert gas and preferably water.

For example, in the stream S0a comprising oxygen, inert gas and preferably water, the weight ratio of inert gas to oxygen may be in the range from 1:1 to 10:1. Preferably, the weight ratio of inert gas to oxygen in stream S0a is in the range from 2.5:1 to 4:1, further preferably in the range from 3:1 to 3.5:1.

For example, in the stream S0a comprising oxygen, inert gas and water, the weight ratio of water to oxygen is in the range from 0.001:1 to 5:1. Preferably, the weight ratio of water to oxygen is in the range from 0.01:1 to 0.5:1, further preferably in the range from 0.02:1 to 0.1:1.

Preferably, in the stream S0a comprising oxygen, inert gas and water, the weight ratio of inert gas to oxygen is in the range from 2.5:1 to 4:1, further preferably in the range from 3:1 to 3.5:1, and at the same time, in each of the two aforementioned cases, the weight ratio of water to oxygen is in the range from 0.01:1 to 0.5:1, further preferably in the range from 0.02:1 to 0.1:1.

With regard to stream S0b, it is preferable that from 80% to 100% by weight, further preferably from 95% to 100% by weight, further preferably from 98% to 100% by weight, further preferably from 99% to 100% by weight, of stream S0b consists of methanol, based in each case on the total weight of stream S0b.

In principle, stream S0a, prior to the contacting with stream S0b in (a), may be at any temperature suitable for the process according to the invention. Preferably, stream S0a, prior to the contacting with stream S0b in (a), is at a temperature in the range from 70 to 100° C., further preferably in the range from 75 to 95° C., further preferably in the range from 80 to 90° C.

Equally, stream S0a, prior to the contacting with stream S0b in (a), may be at any pressure suitable for the process according to the invention. Preferably, stream S0a, prior to the contacting with stream S0b in (a), is at a pressure in the range from 1 to 2 bar, preferably in the range from 1.2 to 1.9 bar, further preferably in the range from 1.4 to 1.8 bar.

Preferably, stream S0a, prior to the contacting with stream S0b in (a), is at a temperature in the range from 70 to 100° C., preferably in the range from 75 to 95° C., further preferably in the range from 80 to 90° C., and at the same time, for each of the temperature ranges mentioned, a pressure in the range from 1 to 2 bar, preferably in the range from 1.2 to 1.9 bar, further preferably in the range from 1.4 to 1.8 bar.

In principle, stream S0b, prior to the contacting with stream S0a in (a), may be at any temperature suitable for the process according to the invention. Preferably, stream S0b, prior to the contacting with stream S0a in (a), is at a temperature in the range from 0 to 100° C., preferably in the range from 15 to 95° C., further preferably in the range from 20 to 90° C.

Equally, stream S0b, prior to the contacting with stream S0a in (a), may be at any pressure suitable for the process according to the invention. Preferably, stream S0b, prior to the contacting with stream S0a in (a), is at a temperature in the range from 1 to 2 bar, further preferably in the range from 1.2 to 1.9 bar, further preferably in the range from 1.4 to 1.8 bar.

Preferably, stream S0b, prior to the mixing with stream S0a in (a), is at a temperature in the range from 0 to 100° C., further preferably in the range from 15 to 95° C., further preferably in the range from 20 to 90° C., and at the same time, for each of the temperature ranges mentioned, a pressure in the range from 1 to 2 bar, further preferably in the range from 1.2 to 1.9 bar, further preferably in the range from 1.4 to 1.8 bar.

The stream S0c obtained in (a) is depleted of inert gas. The term "depleted" as used in the context of the present invention means that the proportion by weight of inert gas, based on the total weight of stream S0c, is less than the proportion by weight of inert gas, based on the total weight of the mixture obtained by mixing S0a and S0b. The term "enriched" as used in this context of the present invention means that the proportion by weight of inert gas, based on the total weight of stream S0c, is greater than the proportion by weight of inert gas by mixing S0a and S0b obtained mixture.

The stream S0c depleted of inert gas consists preferably of 80% to 100% by weight, further preferably of 90% to 100% by weight, further preferably of 95% to 100% by weight, further preferably of 98% to 100% by weight, further preferably of 99% to 100% by weight, of methanol, formaldehyde and preferably water.

Further preferably, the stream S0c depleted of inert gas has an inert gas content of 0% to 1% by weight, further preferably of 0% to 0.1% by weight, further preferably of 0% to 0.01% by weight.

The contacting of S0a and S0b in (a) can be effected in any suitable manner. For example, the contacting of S0a and S0b in (a) can be conducted in a continuous or batchwise or semibatchwise mode of operation, preference being given to a continuous mode of operation. For example, the contacting of S0a and S0b in (a) can be effected in continuous mode in cocurrent flow of S0a and S0b or in countercurrent flow of S0a and S0b. Preferably, the contacting of S0a and S0b in (a) is effected continuously in countercurrent flow of S0a and S0b.

The contacting of S0a and S0b in (a) in countercurrent flow of S0a and S0b can be effected in any suitable apparatus or any suitable combination of apparatuses, preference being given to using at least one column, further preferably one or two columns, further preferably one column. The term "column" as used in the context of present invention is understood to mean a columnar apparatus having separating internals. The term "separating internals" as used in the context of the present invention is understood to mean crossflow or mass transfer trays, for example bubble-cap trays, valve trays, sieve trays, grid trays, dual flow trays, Thormann trays, tunnel-cap trays, and also structured packings and unstructured random packings. Equally conceivable are combinations of at least one tray type and structured packings or random packings or combinations of at least one tray type and structured packings and random packings, in which case the separating internals or combinations of two or more thereof may vary along the longitudinal axis or along the cross section of the column or along the longitudinal axis and along the cross section of the column. Particular preference is given in accordance with the invention to using a column equipped with random packings.

In principle, the at least one column for the contacting of S0a and S0b in (a) is unrestricted in terms of theoretical plates, provided that a stream S0c depleted of inert gas and a stream S0 enriched in inert gas are obtained in (a). Preferably, the at least one column for the contacting of S0a and S0b in (a) has 2 to 20, further preferably 3 to 15, further preferably 4 to 10, further preferably 5 to 7, theoretical plates.

In principle, S0a and S0b can be contacted in (a) at any pressure, provided that a stream S0c depleted of inert gas and a stream S0 enriched in inert gas are obtained in (a). Preferably, S0a and S0b are contacted in (a) at a pressure at the top of the column in the range from 1 to 3 bar, further preferably in the range from 1.2 to 2.5 bar, further preferably in the range from 1.5 to 2 bar.

Equally, S0a and S0b can in principle be contacted in (a) at any temperature, provided that a stream S0c depleted of inert gas and a stream S0 enriched in inert gas are obtained in (a). Preferably, S0a and S0b are contacted in (a) at a temperature in the bottom of the column in the range from 40 to 80° C., further preferably in the range from 45 to 75° C., further preferably in the range from 50 to 70° C.

Preferably, S0a and S0b are contacted in (a) at a pressure at the top of the column in the range from 1 to 3 bar, further preferably in the range from 1.2 to 2.5 bar, further preferably in the range from 1.5 to 2 bar, and at the same time, for each of the pressure ranges mentioned, at a temperature in the bottom of the column in the range from 40 to 80° C., further preferably in the range from 45 to 75° C., further preferably in the range from 50 to 70° C.

In principle, the stream S0 enriched in inert gas can be withdrawn in the rectifying section of the column or from the top of the column. Preferably, stream S0 is withdrawn from the top of the column.

In principle, the stream S0c depleted of inert gas can be withdrawn in the stripping section of the column or from the bottom of the column. Preferably, stream S0c is withdrawn from the bottom of the column.

The stream S0c depleted of inert gas is not restricted in principle with regard to its further use. For example, it is possible that stream S0c is at least partly sent to a process other than that according to the invention. It is likewise possible that at least a portion of stream S0c is fed into the column as reflux. If at least a portion of stream S0c is fed into the column as reflux, this can be done in the stripping section of the column, in the rectifying section of the column or at the top of the column. Preferably, at least a portion of stream S0c is fed into the column as reflux, preferably into the top of the column.

If at least a portion of stream S0c is fed into the column as reflux, preferably into the top of the column, the reflux is not restricted in principle in terms of the temperature prior to feeding, and can be kept constant, heated or cooled after the withdrawal and before the feeding. Preferably, the at least one portion of stream S0c, before being fed in, is heated to a temperature in the range from 80 to 100° C., further preferably in the range from 85 to 99° C., further preferably from 90 to 98° C.

In principle, any desired heat source can be used to heat the at least one portion into the at least one column in (a) recycled stream S0c. For example, all forms of heat exchangers known to those skilled in the art are useful here, for example plate heat exchangers, shell and tube heat exchangers and spiral heat exchangers. Preferably, the at least one portion into the at least one column in (a) recycled stream S0c is heated in an integrated system using at least a portion of at least one further stream in the process according to the invention. Preferably, the energy required to heat the at least one portion of stream S0c recycled is taken from the bottom of the column in (ii), preferably by means of at least one heat exchanger.

Preferably from 50% to 100% by weight, further preferably from 60% to 100% by weight, further preferably from 70% to 99% by weight, of stream S0c is fed in as reflux, preferably into the top of the column.

Removal in (ii)

In (ii), at least a portion of the inert gas present in S1 is removed from at least a portion of the formaldehyde present in S1 by absorbing the formaldehyde in an absorbent to obtain a stream S2 comprising at least a portion of the inert gas, and to obtain a stream S3 comprising absorbent and absorbate comprising formaldehyde.

The term "absorbent" as used in the context of the present invention is an absorbent used within an absorption, in which a compound to be absorbed can be absorbed. The term "absorbate" as used in the context of the present invention is the entirety of the compounds which are absorbed in an absorbent within an absorption. It is preferably a feature of the absorbent that it has an elevated affinity for formaldehyde and therefore absorbs it preferentially (especially with respect to the inert gas) under the absorption conditions. Preference is given in the context of the present invention to an absorbent which leads to an absorption product stream S3 leaving the absorption apparatus under the absorption conditions. This treatment comprises, based on the stream S1 fed to the absorption apparatus present mass flow rate of inert gas, a mass flow rate of inert gas reduced by at least 50%, preferably at least 90%, more preferably at least 99%.

The present invention therefore also relates to the process as described above for preparing acrylic acid from methanol and acetic acid, comprising
(i) contacting a gaseous stream S0 comprising methanol, oxygen and inert gas with an oxidation catalyst to obtain a gaseous stream S1 comprising formaldehyde and inert gas;
(ii) removing at least a portion of the inert gas present in S1 from at least a portion of the formaldehyde present in S1 by absorbing this formaldehyde in an absorbent to obtain a gaseous stream S2 comprising the portion of the inert gas removed, and to obtain a stream S3 comprising absorbent and absorbate comprising formaldehyde;
(iii) optionally removing a portion or the entirety of the absorbent present in stream S3, such that a stream S3a remains from stream S3, and producing a stream S4 from at least stream S3 or stream S3a and a stream S5 comprising acetic acid; and
(iv) contacting stream S4 in gaseous form with an aldol condensation catalyst to obtain a gaseous stream S6 comprising acrylic acid,
wherein, in the absorbate obtained in (ii) and the stream S3 obtained in (ii), the mass flow rate of inert gas based on the stream S1 fed to the absorption apparatus present mass flow rate of inert gas is reduced by at least 50%, preferably at least 90%, more preferably at least 99%.

The removal in (ii) of at least a portion of the formaldehyde present in stream S1 through use of absorbent from at least a portion of the inert gas present in stream S1 offers the advantage over existing processes that the subsequent aldol condensation reaction can be conducted using the reactant stream in undiluted form or with a low level of inert gas, which makes it possible to achieve a higher space-time yield.

Moreover, it has been found in accordance with the invention that the stream obtained from the partial oxidation of methanol may optionally comprise molecular hydrogen. It is preferably a feature of the absorbent that it has an elevated affinity for formaldehyde and therefore absorbs it preferentially over molecular hydrogen under the absorption conditions. Preference is given in the context of the present invention to an absorbent which leads to an absorption product stream S3 leaving the absorption apparatus under the absorption conditions. This treatment comprises, based on the stream S1 fed to the absorption apparatus present mass flow rate of molecular hydrogen, a mass flow rate of molecular hydrogen reduced by at least 50%, preferably at least 90%, more preferably at least 99%.

Thus, the process according to the invention, especially if the process is performed on the industrial scale and using one or more recycling streams, additionally has the advantage that the concentration of molecular hydrogen cannot increase in the system and hence, for example, the risk of an explosive hydrogen/oxygen gas reaction is avoided.

The present invention therefore also relates to the process as described above for preparing acrylic acid from methanol and acetic acid, comprising
(i) contacting a gaseous stream S0 comprising methanol, oxygen and inert gas with an oxidation catalyst to obtain a gaseous stream S1 comprising formaldehyde, inert gas and molecular hydrogen;
(ii) removing at least a portion of the inert gas present in S1 and a portion of the molecular hydrogen present in S1 from at least a portion of the formaldehyde present in S1 by absorbing this formaldehyde in an absorbent to obtain a gaseous stream S2 comprising at least the portion of the inert gas removed and at least the portion of the molecular hydrogen removed, and to obtain a stream S3 comprising absorbent and absorbate comprising formaldehyde;
(iii) optionally removing a portion or the entirety of the absorbent present in stream S3, such that a stream S3a remains from stream S3, and producing a stream S4 from at least stream S3 or stream S3a and a stream S5 comprising acetic acid; and
(iv) contacting stream S4 in gaseous form with an aldol condensation catalyst to obtain a gaseous stream S6 comprising acrylic acid,
wherein, in the absorbate obtained in (ii) and the stream S3 obtained in (ii), the mass flow rate of inert gas based on the stream S1 fed to the absorption apparatus present mass flow rate of inert gas is reduced by at least 50%, preferably at least 90%, more preferably at least 99%, and wherein, in the absorbate obtained in (ii) and the stream S3 obtained in (ii), the mass flow rate of molecular hydrogen based on the stream S1 fed to the absorption apparatus present mass flow rate of molecular hydrogen is reduced by at least 50%, preferably at least 90%, more preferably at least 99%.

In addition, it has been found in accordance with the invention that the stream obtained from the partial oxidation of methanol may optionally comprise unconverted methanol. In the context of the present invention, it is preferable to use an absorbent which, in (ii), under the absorption conditions, absorbs not more than a portion, preferably of 50% to 90% by weight, further preferably of 65% to 90% by weight, further preferably of 80% to 90% by weight, of the methanol present in S1. In this case, it is a feature of the process according to the invention that, in the absorption in (ii), a portion of the methanol present in S1 is discharged via stream S2, and hence stream S3 is depleted of methanol, the result of which is that the subsequent aldol condensation reaction can be conducted with a reactant stream slightly diluted at most by methanol, which makes it possible to achieve a higher space-time yield of target product.

The present invention therefore also relates to the process as described above for preparing acrylic acid from methanol and acetic acid, comprising
(i) contacting a gaseous stream S0 comprising methanol, oxygen and inert gas with an oxidation catalyst to obtain a gaseous stream S1 comprising formaldehyde, inert gas and methanol;
(ii) removing at least a portion of the inert gas present in S1 and at least a portion of the methanol present in S1 from at least a portion of the formaldehyde present in S1 by absorbing this formaldehyde in an absorbent to obtain a gaseous stream S2 comprising at least the portion of the inert gas removed and at least the portion of the methanol removed, and to obtain a stream S3 comprising absorbent and absorbate comprising formaldehyde;

(iii) optionally removing a portion or the entirety of the absorbent present in stream S3, such that a stream S3a remains from stream S3, and producing a stream S4 from at least stream S3 or stream S3a and a stream S5 comprising acetic acid; and (iv) contacting stream S4 in gaseous form with an aldol condensation catalyst to obtain a gaseous stream S6 comprising acrylic acid, wherein, in the absorbate obtained in (ii) and the stream S3 obtained in (ii), the mass flow rate of inert gas based on the stream S1 fed to the absorption apparatus present mass flow rate of inert gas is reduced by at least 50%, preferably at least 90%, more preferably at least 99%, and wherein, in the absorbate obtained in (ii) and the stream S3 obtained in (ii), from 50% to 99% by weight, preferably from 65% to 95% by weight, further preferably from 75% to 90% by weight, of the methanol present in S1 is present.

Accordingly, the present invention also relates to the process as described above for preparing acrylic acid from methanol and acetic acid, comprising (i) contacting a gaseous stream S0 comprising methanol, oxygen and inert gas with an oxidation catalyst to obtain a gaseous stream S1 comprising formaldehyde, inert gas, molecular hydrogen and methanol;

(ii) removing at least a portion of the inert gas present in S1, at least a portion of the molecular hydrogen present in S1 and at least a portion of the methanol present in S1 from at least a portion of the formaldehyde present in S1 by absorbing this formaldehyde in an absorbent to obtain a gaseous stream S2 comprising at least the portion of the inert gas removed, at least the portion of the molecular hydrogen removed and at least the portion of the methanol removed, and to obtain a stream S3 comprising absorbent and absorbate comprising formaldehyde;

(iii) optionally removing a portion or the entirety of the absorbent present in stream S3, such that a stream S3a remains from stream S3, and producing a stream S4 from at least stream S3 or stream S3a and a stream S5 comprising acetic acid; and (iv) contacting stream S4 in gaseous form with an aldol condensation catalyst to obtain a gaseous stream S6 comprising acrylic acid, wherein, in the absorbate obtained in (ii) and the stream S3 obtained in (ii), the mass flow rate of inert gas based on the stream S1 fed to the absorption apparatus present mass flow rate of inert gas is reduced by at least 50%, preferably at least 90%, more preferably at least 99%, and wherein, in the absorbate obtained in (ii) and the stream S3 obtained in (ii), the mass flow rate of molecular hydrogen based on the stream S1 fed to the absorption apparatus present mass flow rate of molecular hydrogen is reduced by at least 50%, preferably at least 90%, more preferably at least 99%, and, in the stream S3 obtained in (ii), from 50% to 90% by weight, preferably from 65% to 90% by weight, further preferably from 80% to 90% by weight, of the methanol present in S1 is present.

In principle, the absorbent is not subject to any particular restriction in terms of its chemical nature, provided that the inventive absorption can be conducted. Preferably, the absorbent in (ii) comprises water or formaldehyde or acetic acid or a mixture of formaldehyde and water or a mixture of formaldehyde and acetic acid or a mixture of acetic acid and water or a mixture of formaldehyde, acetic acid and water. Further preferably, at least 80% by weight, further preferably at least 85% by weight, further preferably at least 90% by weight, of the absorbent, based on the total weight thereof, in (ii), consists of water or of formaldehyde or of acetic acid or of a mixture of formaldehyde and water or of a mixture of formaldehyde and acetic acid or of a mixture of acetic acid and water or of a mixture of formaldehyde, acetic acid and water.

Further preferably, the absorbent in (ii) comprises water, preferably water and formaldehyde. Further preferably, at least 90% by weight, further preferably from 90% to 100% by weight, further preferably from 95% to 100% by weight, of the absorbent in (ii) consists of water and formaldehyde.

Especially in that preferred case in which the absorbent in (ii) comprises water and formaldehyde, it is possible in the process according to the invention for at least a portion of the absorbent used in (ii) to be a constituent of this absorbent recycled from a process step in the process according to the invention downstream of the relevant absorption into the relevant absorption. This has the advantage that there is not necessarily any need to feed water as absorbent to the process according to the invention; instead, for example, water which forms in the aldol condensation in (iv) can be at least a portion of the absorbent used in (ii) given appropriate recycling.

Especially in the preferred case in which the absorbent in (ii) comprises water and formaldehyde, at least a portion of the absorbent is recycled from a step in the process according to the invention downstream of the relevant absorption. This has the advantage that there is not necessarily any need to feed water to the process according to the invention; instead, the water which forms, for example, in the condensation reaction can be used. A further advantage is that it is simultaneously possible to reuse unconverted formaldehyde in the process in a simple manner. In addition, the use of a suitable recycled stream from the process as at least part of the absorbent used in (ii) has the advantage that the water by-product has to be separated from formaldehyde only to a lesser degree.

It is likewise possible for formaldehyde unconverted in the aldol condensation in (iv), given appropriate recycling, to be at least a portion of the absorbent used in (ii). In this way, formaldehyde unconverted in the aldol condensation in (iv) is recycled into the process according to the invention in a comparatively elegant manner and reused for preparation of acrylic acid.

The above finding offers the overall advantage that it is sufficient in accordance with the invention, in the recycling of water by-product and unconverted formaldehyde reactant present in the product mixture from the aldol condensation in (iv) out of this product mixture into the absorbent for absorption in (ii), to remove only a portion of water from the recycled formaldehyde by virtue of this recycling operation.

Preferably, the weight ratio of formaldehyde to water in the absorbent in (ii) is in the range from 0:1 to 2:1, preferably in the range from 0.01:1 to 1:1, further preferably in the range from 0.1:1 to 0.5:1.

With regard to the stream S2 comprising at least a portion of the inert gas obtained in (ii), it is preferable that it consists of inert gas to an extent of at least 70% by weight, further preferably of 75% to 99% by weight, further preferably of 80% to 95% by weight.

Preferably, stream S2 comprises, as well as inert gas, additionally at least one further compound, preferably selected from the group consisting of water, methanol, formaldehyde, carbon dioxide, oxygen and hydrogen.

Optionally, stream S2 comprises, as well as inert gas and the at least one aforementioned compound, at least one further compound, preferably selected from the group consisting of acetaldehyde, methyl acrylate, methyl acetate, ethene, acetone, methyl formate, methylene glycol, hemiformal and carbon monoxide. Preferably, the total content in stream S2 of this at least one compound present in addition to inert gas is not more than 30% by weight, preferably from 1% to 25% by weight, further preferably from 5% to 20% by weight.

With regard to the stream S3 obtained in (ii), it is preferable that this consists of water and formaldehyde, based on its total weight, to an extent of at least 80% by weight, preferably to an extent of at least 90% by weight, further preferably to an extent of 95% to 97% by weight or more.

Preferably, the weight ratio of water to formaldehyde in stream S3 is in the range from 0.75:1 to 1.25:1, preferably in the range from 0.85:1 to 1.15:1, further preferably in the range from 0.95:1 to 1.05:1.

The removal in (ii) can be conducted in any suitable apparatus or in any suitable combination of apparatuses, preference being given to using at least one column, further preferably one or two columns, further preferably one column, which has separating internals in accordance with the invention and in which stream S1 and the absorbent are normally conducted in countercurrent. The absorbent is conducted such that it descends in the column, and stream S1 such that it ascends in the column. Particular preference is given to using an absorption column equipped with random packings as separating internals.

In principle, the at least one column for the removal in (ii) is unrestricted in terms of theoretical plates, provided that a stream S2 comprising at least a portion of the inert gas and a stream S3 comprising formaldehyde are obtained in (ii). Preferably, the at least one column for the removal in (ii) has 4 to 30, further preferably 6 to 20, further preferably 8 to 15, further preferably 10 to 14, theoretical plates.

In principle, the removal in (ii) can be effected at any suitable pressure, provided that a stream S2 comprising at least a portion of the inert gas and a stream S3 comprising formaldehyde are obtained in (ii). Preferably, the removal in (ii) is effected at a pressure at the top of the column in the range from 0.5 to 2 bar, further preferably in the range from 0.75 to 1.5 bar, further preferably in the range from 0.9 to 1.25 bar.

In principle, the separation in (ii) can be effected at any suitable temperature, provided that a stream S2 comprising at least a portion of the inert gas and a stream S3 comprising formaldehyde are obtained in (ii). Preferably, the removal in (ii) is effected at a temperature in the bottom of the column in the range from 60 to 100° C., further preferably in the range from 70 to 90° C., further preferably in the range from 75 to 85° C.

Preferably, the separation in (ii) is conducted at a pressure at the top of the column in the range from 0.5 to 2 bar, further preferably in the range from 0.75 to 1.5 bar, further preferably in the range from 0.9 to 1.25 bar, and at the same time, for each of the pressure ranges mentioned, at a temperature in the bottom of the column in the range from 60 to 100° C., further preferably in the range from 70 to 90° C., further preferably in the range from 75 to 85° C.

In principle, stream S3 can be withdrawn in the stripping section of the column or from the bottom of the column in (ii). Preferably, stream S3 is withdrawn from the bottom of the column in (ii).

In principle, stream S2 can be withdrawn in the rectifying section of the column or from the top of the column in (ii). Preferably, stream S2 is withdrawn from the top of the column in (ii).

The stream S3 withdrawn with preference from the bottom of the column is not restricted in principle in terms of its further use. For example, it is possible that stream S3 is at least partly sent to a process other than that according to the invention. Preference is given to recycling a portion of stream S3 as absorbent into the column in (ii). This recycling can be effected into the stripping section of the column, into the rectifying section of the column or to the top of the column. Preferably, a portion of stream S3, preferably from 75% to 90% by weight, further preferably from 80% to 85% by weight, of stream S3, optionally after cooling to a temperature in the range from 60 to 70° C., preferably in the range from 65 to 70° C., is recycled into the lower part, further preferably into the lowermost liquid distributor, of the column in (ii) as absorbent.

Preferably, a stream is withdrawn from at least one lower part of the column in (ii) and recycled into a part higher up, preferably 1 to 3 theoretical plates higher, there being no restriction in principle in the composition of this stream withdrawn and recycled into a higher part in terms of composition. Preferably, at least 90% by weight, further preferably at least 95% by weight, of the stream withdrawn consists of water and formaldehyde. The stream withdrawn from at least one lower part of the column in (ii) can be recycled into a part higher up or heated or cooled isothermally. Preference is given to cooling the stream withdrawn from at least one lower part of the column in (ii), prior to recycling into the column, to a temperature in the range from 50 to 60° C., preferably in the range from 55 to 60° C.

Preferably, a stream is withdrawn from at least one middle part of the column in (ii) and recycled into a part higher up, preferably 1 to 3 theoretical plates higher, there being no restriction in principle in the composition of this stream withdrawn and recycled into a higher part in terms of composition. Preferably, at least 90% by weight, further preferably at least 93% by weight, of the stream withdrawn consists of water and formaldehyde. The stream withdrawn from at least one middle part of the column in (ii) can be recycled into a part higher up or heated or cooled isothermally. Preference is given to cooling the stream withdrawn from at least one middle part of the column in (ii), prior to recycling, to a temperature in the range from 30 to 40° C., preferably in the range from 35 to 40° C.

As a further integrative measure in the process according to the present invention, preference is given to recycling a stream, which is preferably withdrawn from the absorption columns in (ii) in the liquid phase, as an external reflux into the column used with preference in (a), further preferably into the saturation column used, the effect of which is that this recycling of a stream from the inventive absorption into the upstream stage of partial oxidation of methanol further enhances the overall efficiency of the process, because this adds at least a portion of water to stream S0, which surprisingly enhances the selectivity of the oxidation reaction of methanol to formaldehyde.

Therefore, the process according to the present invention preferably comprises
(a) contacting, preferably in countercurrent, a stream S0a comprising oxygen, inert gas and preferably water with a stream S0b comprising methanol to obtain a stream S0c depleted of inert gas and a stream S0 enriched in inert gas, the contacting in (a) being effected in countercurrent, using one column;

wherein a liquid stream is withdrawn from at least one upper part of the column in (ii) and at least partly recycled into (a), preferably as external reflux into the column, further preferably into the top of the column.

The stream withdrawn from at least one upper part of the column in (ii) is not restricted in principle in terms of its composition. Preferably, at least 90% by weight, further preferably from 90% to 98% by weight, further preferably from 92% to 95% by weight, of the stream withdrawn from the at least one upper part of the column consists of water and formaldehyde.

Production of a Stream S4 in (iii)

In stage (iii) of the process according to the invention, stream S3 and a stream S5 comprising acetic acid are used to produce stream S4, it being possible to produce stream S4 not only with stream S3 and a stream S5 comprising acetic acid but optionally with one or more than one further stream. For example, the streams S4a and S4b described below are suitable as one further or more than one further stream.

With regard to the composition of stream S4, it is preferable that it consists to an extent of at least 95% by weight, further preferably to an extent of 95% to 99% by weight, further preferably to an extent of 96% to 98% by weight, of water, formaldehyde, acetic acid and inert gas, based in each case on the total weight of stream S4.

Preferably, stream S4 comprises up to 90% by weight of inert gas. In a first embodiment, it is further preferable that stream S4 comprises from 0.1% to 10% by weight, further preferably 0.3% to 5% by weight, further preferably 0.4% to 3% by weight, further preferably 0.5% to 1% by weight, of inert gas. In a second embodiment, it is preferable that stream S4 comprises from 10% to 90% by weight, further preferably from 10% to 85% by weight, further preferably from 20% to 80% by weight, further preferably from 30% to 70% by weight, further preferably from 40% to 60% by weight, of inert gas.

Stream S4, which consists to an extent of at least 95% by weight, preferably to an extent of 95% to 99% by weight, further preferably to an extent of 96% to 98% by weight, of water, formaldehyde, acetic acid and inert gas, is likewise not restricted in principle in terms of inert gas content. Preferably, stream S4 comprises up to 90% by weight of inert gas. It is further preferable that stream S4 comprises from 0.1% to 10% by weight, further preferably 0.3% to 5% by weight, further preferably 0.4% to 3% by weight, further preferably 0.5% to 1% by weight, of inert gas. It is likewise further preferable that stream S4 comprises from 10% to 90% by weight, further preferably from 10% to 85% by weight, further preferably from 20% to 80% by weight, further preferably from 30% to 70% by weight, further preferably from 40% to 60% by weight, of inert gas.

Stream S4, which consists to an extent of at least 95% by weight, preferably to an extent of 95% to 99% by weight, further preferably to an extent of 96% to 98% by weight, of water, formaldehyde, acetic acid and inert gas, appropriately in application terms, has a weight ratio of formaldehyde to water which is preferably in the range from 0.75:1 to 3:1, further preferably in the range from 0.85:1 to 2:1, further preferably in the range from 0.95:1 to 1.5:1.

Stream S4, which consists to an extent of at least 95% by weight, preferably to an extent of 95% to 99% by weight, further preferably to an extent of 96% to 98% by weight, of water, formaldehyde, acetic acid and inert gas, appropriately in application terms, has a weight ratio of acetic acid to water which is preferably in the range from 6:1 to 12:1, further preferably in the range from 7:1 to 11:1, further preferably in the range from 8:1 to 10:1.

Preferably, in stream S4, which consists to an extent of at least 95% by weight, preferably to an extent of 95% to 99% by weight, further preferably to an extent of 96% to 98% by weight, of water, formaldehyde, acetic acid and inert gas, the weight ratio of formaldehyde to water is in the range from 0.75:1 to 3:1, further preferably in the range from 0.85:1 to 2:1, further preferably in the range from 0.95:1 to 1.5:1, and at the same time, in each of the cases mentioned, the weight ratio of acetic acid to water is in the range from 6:1 to 12:1, further preferably in the range from 7:1 to 11:1, further preferably in the range from 8:1 to 10:1.

It is conceivable in principle that stream S4 consists of formaldehyde, water and acetic acid. It is possible that stream S4 comprises diluents or carrier gases as further components. Preferably, stream S4 comprises, as well as formaldehyde, water and acetic acid, additionally one or more than one compound selected from the group consisting of acrylic acid, methanol, ethene, carbon dioxide and carbon monoxide, where the total content of these compounds in stream S4 is not more than 10% by weight, preferably from 0.1% to 8% by weight, further preferably from 0.5% to 5% by weight.

Stream S5 used in (iii) comprises acetic acid and serves for production of stream S4. In principle, it is possible that stream S5 is produced from several streams, at least one of which comprises acetic acid. Preferably, stream S5 is produced from a stream S5a comprising acetic acid and a stream S5b comprising acetic acid, at least a portion of stream S5b being a stream recycled from the process beyond (iv).

A stream S5a comprising acetic acid is not restricted in principle in terms of its acetic acid content. Preferably at least 50% by weight, further preferably at least 75% by weight, further preferably at least 85% by weight, further preferably at least 90% by weight, further preferably at least 95% by weight, further preferably from 95% to 100% by weight, of stream S5a consists of acetic acid.

Preferably, a stream S5a comprises, in addition to acetic acid, at least one further compound, preferably selected from the group consisting of water, propionic acid and acrylic acid, preferably water and propionic acid, there being no restriction in principle with regard to the total content of these compounds in a stream S5a. Preferably, the total content of these compounds in a stream S5a is not more than 10% by weight, not more than 5% by weight, further preferably from 0% to 5% by weight.

A stream S5b recycled from the process preferably beyond (iv) is not restricted in principle in terms of the acetic acid content. Preferably at least 50% by weight, further preferably at least 75% by weight, further preferably at least 85% by weight, further preferably at least 90% by weight, further preferably at least 95% by weight, further preferably from 95% to 99% by weight, of a stream S5b recycled from the process beyond (iv) consists of acetic acid.

Preferably, a stream S5b comprises, in addition to acetic acid, one or more than one further compound, preferably selected from the group consisting of water and acrylic acid. Preferably, a stream S5b comprises, in addition to acetic acid, also water and acrylic acid. Further preferably, the total content of water and acrylic acid in a stream S5b is not more than 5% by weight, preferably from 0.5% to 5% by weight, further preferably from 1% to 4% by weight.

As described above, stream S4 in (iii), as well as a stream S3 comprising absorbent and absorbate comprising formaldehyde and a stream S5 comprising acetic acid, is additionally produced with one or more than one further stream. Preferably, in (iii), a stream S4a preferably comprising inert gas, carbon dioxide and carbon monoxide is used as one or more than one further stream. It is further preferable here that at least a portion of a stream S4a is a stream recycled from the process beyond (iv).

A stream S4a which comprises inert gas, carbon dioxide and carbon monoxide and has been recycled from the process beyond (iv) is not restricted in principle in terms of its composition. Preferably at least 80% by weight, further preferably from 80% to 95% by weight, further preferably from 85% to 90% by weight, of a stream S4a recycled from the process beyond (iv) consists of inert gas, carbon dioxide and carbon monoxide.

It is conceivable in principle that a stream S4a consists of inert gas, carbon dioxide and carbon monoxide. Preferably, stream S4a additionally comprises one or more than one further compound, preferably selected from the group consisting of water, formaldehyde, acetaldehyde, methanol, methyl acrylate, methyl acetate, ethene, acetone, methyl formate, methylene glycol and hemiformal. Preferably, the total content of these compounds in stream S4a is not more than 20% by weight, further preferably from 5% to 20% by weight, further preferably from 5% to 10% by weight.

Further preferably, stream S4 is produced from stream S3, stream S5, preferably a stream S4a comprising inert gas, carbon dioxide and carbon monoxide, and additionally one or more than one, preferably one, inert gas stream S4b. In principle, useful inert gases in this context of the present invention are all inert materials that are gaseous under the process conditions, the term "inert gas" comprising a single gas or a mixture of two or more gases. For example, useful inert gases include helium, neon, argon, krypton, radon, xenon, nitrogen, sulfur hexafluoride and gas mixtures of two or more thereof. Preferably, the inert gas in stream S4b comprises nitrogen, there being no restrictions in principle with regard to the content of nitrogen. Preferably, at least 75% by weight, further preferably at least 80% by weight, further preferably at least 90% by weight, of the inert gas in stream S4b consists of nitrogen.

Contacting in (iv)

In stage (iv) of the process according to the invention, stream S4, preferably in gaseous form, is contacted with an aldol condensation catalyst, preferably in solid form, to obtain a gaseous stream S6 comprising acrylic acid.

The term "aldol condensation catalyst" as used in this context of the present application is understood to mean any catalyst capable of catalyzing an aldol condensation of the two compounds formaldehyde and acetic acid to give acrylic acid.

In principle, all suitable aldol condensation catalysts are useful in accordance with the invention. Examples, used as unsupported catalysts or in supported form, are alkali metal or alkaline earth metal oxides, mixed oxides comprising vanadium oxide, aluminosilicates or zeolites. Preferably, the aldol condensation catalyst in (iv) comprises vanadium and optionally phosphorus, further preferably vanadium and phosphorus, further preferably a vanadium-phosphorus oxide. Further preferably, the aldol condensation catalyst in (iv) comprises a vanadium-phosphorus oxide having the general empirical formula $V_2O_x(PO_4)_y$, where x is preferably in the range from 1.0 to 2.75, further preferably from 1.5 to 2.25, and y is preferably in the range from 1.5 to 2.5, further preferably from 1.8 to 2.3.

Preferably, the aldol condensation catalyst in (iv) is in the form of an unsupported catalyst or in supported form on at least one support material. If the aldol condensation catalyst in (iv) is present in supported form on at least one support material, the at least one support material is preferably selected from the group consisting of $SiO_2$, $TiO_2$, $Al_2O_3$ and $ZrO_2$ and mixtures of two or more thereof. Preferably, the aldol condensation catalyst in (iv) is used as an unsupported catalyst.

The aldol condensation catalyst in (iv) may be present, for example, as granules or extrudates in the form of cylinders, spheres, hollow cylinders, in star form, in tablet form or as a mixture thereof. Preferably, the aldol condensation catalyst in (iv) is in the form of extrudates, the cross section of the extrudates having a rectangular, triangular, hexagonal, square, polygonal, oval or circular shape. Particular preference is given to using an aldol condensation catalyst in extrudates with a round cross section, the diameter of the round cross-sectional area being in the range from 0.1 to 100 mm, preferably in the range from 0.2 to 80 mm, further preferably in the range from 0.5 to 50 mm, further preferably in the range from 1 to 30 mm, and at the same time, for each of the aforementioned cases, the length of the extrudates being in the range from 0.1 to 100 mm, preferably in the range from 0.5 to 80 mm, further preferably in the range from 1 to 70 mm.

The contacting in (iv) is preferably effected in at least one reactor, further preferably in at least two reactors, for example two, three, four or five reactors, where at least two reactors may be arranged in parallel or at least two reactors in series or at least two reactors in parallel and at least two reactors in series.

It is likewise possible that at least two, preferably two, three, four or five, further preferably two, three or four, further preferably two or three, further preferably two, reactors connected in parallel are used in alternation, with at least one reactor always in operation in this alternating mode of operation. Preferably, the contacting in (iv) is effected in at least one reactor, preferably at least two reactors, further preferably in at least two reactors connected in parallel, which are further preferably operated in alternation. Preferably, these reactors are configured as fixed bed reactors, for example as shell and tube reactors or thermoplate reactors. In the case of a shell and tube reactor, the catalytically active fixed bed is advantageously within the catalyst tubes, with fluid heat carrier flowing around them.

The catalyst hourly space velocity with regard to the contacting in (iv) in the reactor is preferably chosen such that a balanced ratio of the parameters of conversion, selectivity, yield, reactor geometry and reactor dimensions can be achieved, the catalyst hourly space velocity with regard to the contacting in (iv) in the reactor being defined as mass of S4 in kg per hour and per unit mass of aldol condensation catalyst in kg. Preferably, the contacting in (iv) in the fixed bed reactor is effected at a catalyst hourly space velocity in the range from 0.01 to 50 kg/(h*kg), further preferably in the range from 0.1 to 40 kg/(h*kg), further preferably in the range from 0.5 to 30 kg/(h*kg).

The contacting in (iv) in the reactor is not subject to any particular restrictions with regard to the temperature of the catalyst bed, provided that the contacting of stream S4 with the aldol condensation catalyst in (iv) gives a stream S6 comprising acrylic acid. Preferably, the contacting in (iv) in the reactor is effected at a temperature of the catalyst bed in the range from 200 to 450° C., further preferably in the range from 250 to 400° C., further preferably in the range from 290 to 380° C.

The contacting in (iv) is not subject to any particular restrictions with regard to the pressure in the reactor, provided that the contacting of stream S4 with the aldol condensation catalyst in (iv) gives a stream S6 comprising acrylic acid. Preferably, the contacting in (iv) in the reactor is effected at a pressure in the range from 0.5 to 5 bar, further preferably range from 0.8 to 3 bar, further preferably range from 1 to 1.8 bar.

Preferably, the contacting in (iv) in the reactor is effected at a temperature of the catalyst bed in the range from 200 to 450° C., further preferably in the range from 250 to 400° C., further preferably in the range from 290 to 380° C., and at the same time, for each of the aforementioned temperature ranges, a pressure in the range from 0.5 to 5 bar, further preferably range from 0.8 to 3 bar, further preferably range from 1 to 1.8 bar.

It is conceivable in principle that the stream S6 obtained in (iv) consists of acrylic acid. Preferably, the stream S6 obtained in (iv) comprises acrylic acid and one or more than one further compound, further preferably acrylic acid and formaldehyde, further preferably acrylic acid, formaldehyde and water, further preferably acrylic acid, formaldehyde, water and acetic acid, further preferably acrylic acid, formaldehyde, water, acetic acid and inert gas.

Preferably at least 90% by weight, further preferably from 95% to 99% by weight, further preferably from 96% to 98% by weight, of stream S6 consists of acrylic acid, formaldehyde, water, acetic acid and inert gas.

In a first embodiment, it is further preferable that stream S6 comprises inert gas to an extent of 0.1% to 10% by weight, further preferably to an extent of 0.3% to 5% by weight, further preferably to an extent of 0.4% to 3% by weight, further preferably to an extent of 0.5% to 1% by weight of its weight. In a second embodiment, it is further preferable that stream S6 comprises inert gas to an extent of 10% to 90% by weight, further preferably to an extent of 10% to 85% by weight, further preferably to an extent of 20% to 80% by weight, further preferably to an extent of 30% to 70% by weight, further preferably to an extent of 40% to 60% by weight of its weight.

The stream S6 obtained in (iv) preferably has a weight ratio of acrylic acid to water in the range from 1.0:1 to 2.0:1, further preferably in the range from 1.05:1 to 1.75:1, further preferably in the range from 1.1:1 to 1.5:1.

The weight ratio of acrylic acid to acetic acid in stream S6 is preferably in the range from 0.1:1 to 0.75:1, further preferably in the range from 0.15:1 to 0.5:1, further preferably in the range from 0.2:1 to 0.25:1.

With regard to the weight ratio of acrylic acid to formaldehyde in stream S6, it is preferably in the range from 4:1 to 9:1, further preferably in the range from 5:1 to 8:1, further preferably in the range from 6:1 to 7:1.

Preferably, in stream S6, the weight ratio of acrylic acid to water in stream S6 is in the range from 1.0:1 to 2.0:1, further preferably in the range from 1.05:1 to 1.75:1, further preferably in the range from 1.1:1 to 1.5:1, the weight ratio of acrylic acid to acetic acid in all the aforementioned cases is at the same time in the range from 0.1:1 to 0.75:1, further preferably in the range from 0.15:1 to 0.5:1, further preferably in the range from 0.2:1 to 0.25:1, and the weight ratio of acrylic acid to formaldehyde in all the aforementioned cases is at the same time in the range from 4:1 to 9:1, further preferably in the range from 5:1 to 8:1, further preferably in the range from 6:1 to 7:1.

It is conceivable in principle that the stream S6 obtained in (iv) consists of acrylic acid, water, formaldehyde, acetic acid and inert gas. Preferably, stream S6 additionally comprises one or more than one further compound, preferably selected from the group consisting of acetaldehyde, methanol, methyl acrylate, methyl acetate, ethene, acetone, carbon dioxide and carbon monoxide. Preferably, the total content in stream S6 of this additional one or more than one further compound is not more than 10% by weight, preferably from 0.1% to 8% by weight, further preferably from 0.5% to 5% by weight.

The stream S6 obtained in (iv) may in principle be at any temperature. Preferably, the stream S6 obtained in (iv) is at a temperature in the range from 200 to 450° C., further preferably in the range from 250 to 400° C., further preferably in the range from 290 to 380° C.

If achievable, stream S6 can be used further at the temperature specified. In the process according to the invention, it is preferable that the stream S6 obtained in (iv) at a temperature in the range from 200 to 450° C., preferably in the range from 250 to 400° C., further preferably in the range from 290 to 380° C., is first suitably cooled to a temperature in the range from 80 to 190° C., preferably in the range from 90 to 180° C., further preferably in the range from 100 to 150° C. The heat released in the course of this cooling can be utilized suitably in the process.

In one embodiment of the process according to the invention, the stream S6 obtained in (iv), either without prior cooling or after prior cooling as described above, is stored intermediately in one or more buffer vessels, preferably in one buffer vessel, before it is used further. One reason why intermediate storage is preferable in accordance with the invention is in order to balance out any possible slight variations in the composition of stream S6 which may occur in the course of operation of the overall process, which is preferably continuous in accordance with the invention, and thus to ensure that a downstream process stage is supplied continuously with a stream having a comparatively more constant composition over time. According to the design of the overall process, it is preferable, for example, to intermediately store an amount of stream S6 which occurs over a period in the range from 1 to 20 h, preferably from 5 to 15 h, further preferably from 8 to 12 h, in one or more than one buffer vessel. The one or more than one buffer vessel is generally kept at the feed temperature or a temperature below the feed temperature.

Removal in (v)

In general, the stream S6 obtained in (iv), optionally after cooling and/or intermediate storage in one or more buffer vessels, is sent to a further process stage, in order to remove, in an appropriate manner in application terms, any water present and/or any water and formaldehyde present alongside acrylic acid in stream S6 from acrylic acid in this at least one process stage, which gives rise to a stream S8 enriched in acrylic acid compared to stream S6. It is further preferable that, in this additional process stage, as well as stream S8, a stream S7 depleted of acrylic acid compared to stream S6 is formed.

The term "enriched" as used in the context of the present invention means that the proportion by weight of acrylic acid, based on the total weight of stream S8, is greater than the proportion by weight of acrylic acid based on the total weight of stream S6. The term "depleted" as used in the context of the present invention means that the proportion by weight of acrylic acid, based on the total weight of stream S7, is less than the proportion by weight of acrylic acid based on the total weight of stream S6.

The present invention therefore also relates to a process as described above, additionally comprising (v) removing at least a portion of the formaldehyde present in S6, preferably at least a portion of the formaldehyde and water present in S6, from at least a portion of the acrylic acid present in S6 to obtain an acrylic acid-depleted stream S7 comprising formaldehyde, preferably formaldehyde and water, and to obtain a formaldehyde-depleted, preferably formaldehyde- and water-depleted stream S8 comprising acrylic acid.

It is conceivable in principle that stream S7 consists of formaldehyde, preferably formaldehyde and water. Preferably, stream S7 additionally comprises one or more than one further compound, for example inert gas. Preferably, at least 90% by weight, preferably from 90% to 97% by weight, further preferably from 90% to 95% by weight, of stream S7 consists of formaldehyde, water and inert gas.

Preferably, stream S7 comprises up to 90% by weight of inert gas based on its total weight. In a first embodiment, it is further preferable that stream S7, on the same basis, comprises from 0.1% to 10% by weight, further preferably from 0.3% to 5% by weight, further preferably from 0.4% to 3% by weight, further preferably 0.5% to 1% by weight, of inert gas. In a second embodiment, it is further preferable that stream S7, based on its total weight, comprises from 10% to 90% by weight, further preferably from 10% to 85% by weight, further preferably from 20% to 80% by weight, further preferably from 30% to 70% by weight, further preferably from 40% to 60% by weight, of inert gas.

Preferably, the weight ratio of formaldehyde to water in stream S7 is in the range from 0.05:1 to 1:1, further preferably in the range from 0.05:1 to 0.5:1, further preferably in the range from 0.1:1 to 0.4:1.

It is conceivable in principle that stream S7 consists of formaldehyde, water and inert gas. Preferably, stream S7 additionally comprises at least one further compound, preferably selected from the group consisting of acrylic acid, acetic acid, acetaldehyde, methanol, methyl acrylate, methyl acetate, ethene, acetone, methyl formate, carbon dioxide and carbon monoxide. The total content in stream S7 of this additional at least one compounds is, based on its total weight, preferably not more than 10% by weight, further preferably from 3% to 10% by weight, further preferably from 5% to 10% by weight.

It is conceivable in principle that stream S8 consists of acrylic acid. Preferably, stream S8 additionally comprises at least one further compound, preferably selected from the group consisting of acetic acid, water and a mixture thereof. Preferably, at least 90% by weight, preferably from 90% to 100% by weight, further preferably from 95% to 100% by weight, of stream S8 consists of acrylic acid and acetic acid.

Preferably, in stream S8, the weight ratio of acrylic acid to acetic acid is in the range from 0.05:1 to 1:1, preferably in the range from 0.05:1 to 0.5:1, further preferably in the range from 0.1:1 to 0.3:1.

Optionally, the stream S8 obtained in (v) also comprises water in addition to acrylic acid and acetic acid. Preferably, the water content of stream S8 is not more than 5% by weight, preferably from 0% to 5% by weight, further preferably from 0% to 2% by weight.

With regard to the removal in (v), this can be effected by any suitable method or combination of methods. Preferably, the removal in (v) is effected by rectification. For rectificative removal, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays as separating internals.

In principle, the at least one column for the removal in (v) is not restricted in terms of theoretical plates, provided that the described removal in (v) is achieved. Preferably, the at least one column has 30 to 100, preferably 40 to 80, further preferably 50 to 70, further preferably 55 to 65, theoretical plates.

In principle, the removal in (v) can be effected at any suitable pressure. Preferably, the removal in (v) is effected at a pressure at the top of the column in the range from 0.05 to 6 bar, further preferably in the range from 0.2 to 4 bar, further preferably in the range from 0.5 to 2 bar.

Equally, the removal in (v) can in principle be effected at any suitable temperature. Preferably, the removal in (v) is effected at a temperature in the bottom of the column in the range from 50 to 200° C., further preferably in the range from 80 to 180° C., further preferably in the range from 100 to 150° C.

Preferably, the separation in (v) is conducted at a pressure at the top of the column in the range from 0.05 to 6 bar, further preferably in the range from 0.2 to 4 bar, further preferably in the range from 0.5 to 2 bar, and at the same time, for each of the pressure ranges mentioned, at a temperature in the bottom of the column in the range from 50 to 200° C., further preferably in the range from 80 to 180° C., further preferably in the range from 100 to 150° C.

In principle, stream S8 can be withdrawn in the stripping section of the column, in the rectifying section of the column or from the bottom of the column. Preferably, stream S8 is withdrawn from the bottom of the column.

The stream S8 withdrawn with preference from the bottom of the column in (v) is not restricted in principle with regard to its further use. For example, it is possible to send stream S8 to a process other than that according to the invention. It is preferable to recycle a portion of stream S8, optionally after heating and/or at least partial evaporation, preferably after at least partial evaporation, into the process according to the invention, preferably into the column used with preference in (v), preferably into the bottom of the column. Preferably, a portion of stream S8, after at least partial evaporation, is recycled into the bottom of the column, with no restriction in principle on the evaporation rate used for recycling. Preferably, the evaporation rate used for recycling is in the range from 1% to 40%, further preferably from 2% to 30%, further preferably from 3% to 25%, further preferably from 4% to 20%, further preferably from 5% to 15%.

The term "evaporation rate" as used in the context of the present invention refers to the mass-based proportion of a stream which is recycled in gaseous form from the evaporator into the appropriate column, based on the total mass of the stream fed in liquid form from the appropriate column to the evaporator (bottom).

Removal in (vi)

Preferably, the stream S8 obtained in (v) is sent to at least one further process stage, it being preferable to obtain, in this at least one process stage, a stream enriched once again with respect to acrylic acid compared to S8.

The present invention therefore also relates to a process comprising (v) as described above, additionally comprising
(vi) removing at least a portion of the acrylic acid present in S8 to obtain a stream S9 depleted in acrylic acid compared to S8 and at least one stream S10 enriched in acrylic acid compared to S8.

The stream S9 obtained in (vi) is depleted of acrylic acid. The term "depleted" as used in the context of the present invention means that the proportion by weight of acrylic acid, based on the total weight of stream S9, is less than the proportion by weight of acrylic acid based on the total weight of stream S8. The term "enriched" as used in the context of the present invention means that the proportion by weight of acrylic acid, based on the total weight of stream S10, is greater than the proportion by weight of acrylic acid based on the total weight of stream S8.

Preferably, the stream S9 obtained in (vi) comprises acetic acid and water. It is conceivable in principle that stream S9 consists of acetic acid and water. Preferably, at least 95% by weight, preferably from 95% to 99% by weight, further preferably from 96% to 98% by weight, of stream S9 consists of acetic acid and water.

Preferably, the stream S9 obtained in (vi), preferably comprising acetic acid and water, additionally comprises at least one further compound, preferably at least acrylic acid. Preferably, the total acrylic acid content in stream S9 is not more than 5% by weight, further preferably from 1% to 5% by weight, further preferably from 1% to 4% by weight.

In (vi), at least one stream S10 enriched in acrylic acid and/or acrylic acid adducts compared to S8 is obtained. This at least one stream may consist of one or more individual streams. In the context of the present invention, the at least one stream S10 preferably consists of at least two individual streams, further preferably at least the gaseous stream S10a and the liquid stream S10b. As described below, these two individual streams are preferably withdrawn from the stripping section or from the bottom of a column, preferably from the bottom of a column, preferably from the bottom of a rectification column.

The term "acrylic acid adducts" as used in the context refers to components formed reversibly, preferably components formed reversibly and having a higher standard boiling point of acrylic acid, which formed through dimerization or oligomerization of acrylic acid and/or.

Preferably, at least 90% by weight, preferably from 95% to 99.9% by weight, further preferably from 98% to 99.5% by weight, of the total weight of stream S10a consists of acrylic acid. Preferably, stream S10a comprises at least one further compound, preferably acetic acid. Preferably, the acetic acid content of stream S10a is not more than 10% by weight, preferably from 0.1% to 5% by weight, further preferably from 0.2% to 2% by weight.

The liquid stream S10b obtained with preference in (vi) comprises, in addition to acrylic acid, for example, dimers and oligomers of acrylic acid. Preferably, at least 90% by weight, preferably from 90% to 99.9% by weight, further preferably from 95% to 99.9% by weight, of the liquid stream S10b consists of acrylic acid, diacrylic acid and acrylic acid oligomers.

In addition, the liquid stream S10b may comprise, for example, acetic acid. Preferably, the acetic acid content of the liquid stream S10b is, based on its total weight, not more than 1% by weight, preferably from 0.1% to 1% by weight, further preferably from 0.1% to 0.5% by weight.

With regard to the removal in (vi), this can be effected by any suitable method or combination of methods. Preferably, the removal in (vi) is effected by rectification. For rectificative removal, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays, preferably dual flow trays, as separating internals. In principle, the at least one column for the removal in (vi) is not restricted in terms of theoretical plates, provided that the described removal in (vi) is achieved. Preferably, the at least one column for the removal in (vi) has 5 to 50, preferably 10 to 40, further preferably 20 to 30, further preferably 23 to 27, theoretical plates.

In principle, the removal in (vi) can be effected at any suitable pressure. Preferably, the removal in (vi) is effected at a pressure at the top of the column in the range from 0.01 to 0.5 bar, preferably in the range from 0.02 to 0.2 bar, further preferably in the range from 0.03 to 0.15 bar.

Equally, the removal in (vi) can in principle be effected at any suitable temperature. Preferably, the removal in (vi) is effected at a temperature in the bottom of the column in the range from 50 to 120° C., preferably in the range from 60 to 110° C., further preferably in the range from 70 to 100° C.

Preferably, the separation in (v) is conducted at a pressure at the top of the column in the range from 0.01 to 0.5 bar, preferably in the range from 0.02 to 0.2 bar, further preferably in the range from 0.03 to 0.15 bar, and at the same time, for each of the pressure ranges mentioned, at a temperature in the bottom of the column in the range from 50 to 120° C., preferably in the range from 60 to 110° C., further preferably in the range from 70 to 100° C.

In principle, stream S10a can be withdrawn in the stripping section of the column, in the rectifying section of the column or from the bottom of the column. Preferably, stream S10a is withdrawn as a side draw, preferably as a gaseous side draw, from the column, further preferably as a gaseous side draw in the stripping section of the column.

In principle, the stream S10a withdrawn from the column in (vi) as a gaseous side draw in the stripping section of the column is not restricted in terms of its further use. For example, it is possible to commercially utilize stream S10a as a crude acrylic acid stream, to send it to a process other than that according to the invention or to upgrade it through one more than one further process step to give a glacial acrylic acid stream. Useful upgrading methods include, for example, a rectificative fine purification, a crystallization or an azeotropic distillation using one or more than one suitable auxiliary.

The stream S10b withdrawn in liquid form from the bottom of the column in (vi) is not restricted in principle in terms of its further use. For example, it is possible to send stream S10b to a process other than that according to the invention. It is preferable to recycle a portion of stream S10b, optionally after heating and/or at least partial evaporation, preferably after at least partial evaporation, into the process according to the invention, preferably into the bottom of the column in (vi). Further preferably, a portion of stream S10b, after at least partial evaporation, is recycled into the bottom of the column in (vi). The evaporation rate used for recycling is not restricted in principle. Preferably, the evaporation rate used for recycling is in the range from 1% to 40%, further preferably from 2% to 30%, further preferably from 3% to 25%, further preferably from 4% to 20%, further preferably from 5% to 15%.

The stream S10b withdrawn in liquid form from the bottom of the column in (vi), prior to the recycling into the bottom of the column in (vi) which follows at least partial evaporation, can be fed to one or more than one further process step, in order to dissociate any dimers and/or oligomers of acrylic acid present to acrylic acid. For dissociation of any dimers and/or oligomers of acrylic acid present in stream S10b, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays, preferably dual flow trays, as separating internals.

The stream S9 obtained in (vi) can in principle be withdrawn in the stripping section of the column in (vi), in the rectifying section of the column in (vi) or from the top of the column in (vi). Preferably, stream S9 is withdrawn from the top of the column in (vi).

Preferably, a first portion of the stream S9 withdrawn from the top of the column in (vi) is recycled in condensed form into the top of the column in (vi) as reflux, the reflux ratio being unrestricted in principle. Preferably, from 55% to 70% by weight, further preferably from 60% to 65% by weight, of the total amount of stream S9 is recycled in condensed form into the top of the column in (vi) as reflux. Further preferably, from 55% to 70% by weight, further preferably from 60% to 65% by weight, of the total amount of stream S9, after condensation and cooling to a temperature in the range from 30 to 45° C., preferably in the range from 35 to 40° C., is recycled into the top of the column in (vi) as reflux.

Preferably, at least 98% by weight, further preferably at least 99% by weight, further preferably at least 99.9% by weight, of the portion of stream S9 recycled into the top of the column in (vi) after condensation and cooling consists of acetic acid, acrylic acid and water. Preferably, the acetic acid content in stream S9 is at least 95% by weight, further preferably at least 96% by weight, further preferably at least 97% by weight.

It is preferable to recycle stream S9, further preferably one or more than one further portion of stream S9, into the process according to the invention. It is further preferable to recycle one or more than one further portion of stream S9 into a preceding step of the process. It is especially preferable to use one or more than one further portion of stream S9 to produce the above-described stream S5. As likewise described above, it is preferable in accordance with the invention to produce stream S5 from a stream S5a comprising acetic acid and from a stream S5b comprising acetic acid, at least a portion of stream S5b being a stream recycled from the process. This at least one portion of stream S5b which is a stream recycled from a process is more preferably said one or more than one further portion of stream S9.

As one or more than one further portion of stream S9, preferably from 30% to 45% by weight, further preferably from 35% to 40% by weight, of stream S9 is recycled into the process as stream S5b.

It is further preferable to condense this one or more than one further portion of stream S9 prior to use as stream S5b, and preferably to cool it down to a temperature in the range from 30 to 45° C., further preferably in the range from 35 to 40° C.

As described above, the process according to the invention preferably comprises
(v) removing at least a portion of the formaldehyde present in S6, preferably at least a portion of the formaldehyde and water present in S6, from at least a portion of the acrylic acid present in S6 to obtain an acrylic acid-depleted stream S7 comprising formaldehyde, preferably formaldehyde and water, and to obtain a formaldehyde-depleted, preferably formaldehyde- and water-depleted stream S8 comprising acrylic acid.

While stream S8 is preferably fed to the removal stage (vi) as described above, the stream S7 obtained in (v) is wholly or partly recycled into the process according to the invention. It is preferable to recycle a portion of the stream S7 obtained in (v) into the process according to the invention. It is especially preferable to use a portion of stream S7 to produce the above-described stream S4. As likewise described above, it is preferable in accordance with the invention to produce stream S4 in (iii) from stream S3, a stream S5 comprising acetic acid and additionally at least one stream S4a comprising inert gas, carbon dioxide and carbon monoxide, at least one portion of stream S4a being a stream recycled from the process. This at least one portion of stream S4a which is a stream recycled from a process is more preferably said portion of stream S7, stream 7a.

As stream S7a, in a first embodiment, preferably from 2% to 10% by weight, further preferably from 2% to 8% by weight, of stream S7, based on the total amount thereof, is recycled into the process as stream S4a. In a further embodiment, as stream S7a, preferably from 10% to 90% by weight, further preferably from 30% to 80% by weight, of stream S7, based on the total amount thereof, is recycled into the process as stream S4a.

Preferably, stream S7a comprises inert gas, carbon dioxide and carbon monoxide; further preferably, at least 80% by weight, preferably from 80% to 95% by weight, further preferably from 85% to 90% by weight, of stream S7a consists of inert gas, carbon dioxide and carbon monoxide. Preferably, stream S7a additionally comprises at least one further compound, preferably selected from the group consisting of water, formaldehyde, acetaldehyde, methanol, methyl acrylate, methyl acetate, ethene, acetone, methyl formate, methylene glycol and hemiformal. Preferably, the total content of this at least one further compound in stream S7a is not more than 20% by weight, preferably from 5% to 20% by weight, further preferably from 5% to 10% by weight.

Preferably, stream S7a is obtained as an uncondensed portion of stream S7 by cooling stream S7 down to a temperature in the range from 30 to 50° C., preferably in the range from 35 to 45° C. Further preferably, stream S7a, before being recycled into the process as stream S4a, is heated to a temperature in the range from 150 to 300° C., preferably in the range from 200 to 280° C. Accordingly, it is preferable to obtain stream S7a as an uncondensed portion of stream S7 by cooling stream S7 down to a temperature in the range from 30 to 50° C., preferably in the range from 35 to 45° C., and, before recycling it into the process as stream S4a, to heat it to a temperature in the range from 150 to 300° C., preferably in the range from 200 to 280° C.

Preferably, stream S7a, before being recycled into the process as stream S4a, is suitably compressed, preferably to a pressure in the range from 0.95 to 2 bar, preferably in the range from 1 to 1.5 bar.

It is preferable in accordance with the invention to obtain one or more than one condensed portion of stream S7, at least one stream S7b, by cooling stream S7 down to a temperature in the range from 30 to 50° C., preferably in the range from 35 to 45° C. It is preferable to recycle this one or more than one condensed portion of stream S7, stream S7b, into the top of the column used with preference in (v) as external reflux. Further preferably, as stream S7b, from 65% to 80% by weight, further preferably from 70% to 75% by weight, based in each case on the total amount of the one or more than one condensed portion of stream S7, is recycled into the top of the column in (v) as external reflux. Further preferably, as stream S7b, from 65% to 80% by weight, further preferably from 70% to 75% by weight, based in each case on the total amount of the one or more than one portion of stream S7, preferably after cooling to a temperature in the range from 30 to 50° C., further preferably in the range from 35 to 45° C., is recycled into the top of the column in (v) as external reflux.

Preferably, stream S7b comprises formaldehyde and water. Further preferably, at least 90% by weight, preferably from 90% to 99% by weight, further preferably from 95% to 98% by weight, of stream S7b consists of formaldehyde and water.

Preferably, the weight ratio of formaldehyde to water in stream S7b is in the range from 0.05:1 to 1:1, further preferably in the range from 0.05:1 to 0.5:1, further preferably in the range from 0.1:1 to 0.4:1.

Preferably, stream S7b additionally comprises at least one further compound, preferably selected from the group consisting of acrylic acid, acetic acid, acetaldehyde, methanol, methyl acrylate, methyl acetate, ethene, acetone, methyl formate and a mixture of two or more thereof. Preferably, the total content of this at least one further compounds in stream S7b is not more than 10% by weight, further preferably from 1% to 9% by weight, further preferably from 2% to 5% by weight.

Removal in (vii)

In the context of the present invention, it is further preferable to feed one or more than one further portion of stream S7, a stream S7c, to a further process stage in which a stream S11 enriched in formaldehyde and a stream S12 depleted of formaldehyde are obtained. The additional advantage of this further removal stage is considered to be the fact that the stream S11 enriched in formaldehyde, as described below, can be recycled into the process according to the invention and hence the overall efficiency of the process can be enhanced once again.

The present invention therefore also relates to an inventive process comprising (v) as described above, additionally comprising (vii) separating stream S7c into a formaldehyde-enriched stream S11 and a formaldehyde-depleted stream S12, wherein stream S7c is a portion of the one or more than one condensed portion of stream S7 obtained by cooling stream S7, preferably from 10% to 33% by weight, further preferably from 20% to 26% by weight, of the total amount of the one or more than one condensed portion of stream S7 obtained by cooling stream S7.

The stream S11 obtained in (vii) is enriched in formaldehyde compared to S7c. The term "enriched" as used in the context of the present invention means that the proportion by weight of formaldehyde, based on the total weight of stream S11, is greater than the proportion by weight of formaldehyde based on the total weight of stream S7c. The term "depleted" as used in the context of the present invention means that the proportion by weight of formaldehyde, based on the total weight of stream S12, is less than the proportion by weight of formaldehyde based on the total weight of stream S7c.

Preferably, at least 90% by weight, further preferably from 90% to 98% by weight, further preferably from 90% to 95% by weight, of stream S11 consists of formaldehyde and water.

Preferably, the weight ratio of formaldehyde to water in this stream S11 is in the range from 0.25:1 to 1:1, preferably in the range from 0.3:1 to 0.8:1, further preferably in the range from 0.35:1 to 0.5:1.

Preferably, stream S11 additionally comprises at least one further compound, preferably selected from the group consisting of acrylic acid, acetaldehyde, methanol, methyl acrylate, methyl acetate, ethene, acetone, methyl formate and a mixture of two or more thereof. Preferably, the total content of this at least one further compounds in stream S11 is not more than 10% by weight, further preferably from 2% to 10% by weight, further preferably from 5% to 10% by weight.

Preferably, at least 98% by weight, further preferably from 98% to 99.9% by weight, further preferably from 99% to 99.9% by weight, of stream S12 consists of water and formaldehyde.

Preferably, this stream S12 comprises at least one further compound, preferably selected from the group consisting of acrylic acid, acetic acid, methanol and a mixture of two or more thereof. Preferably, the total content of this at least one further compounds in stream S12 is not more than 2% by weight, preferably from 0.1% to 2% by weight, further preferably from 0.1% to 1% by weight.

With regard to the removal in (vii), this can be effected by any suitable method or combination of methods. Preferably, the removal in (vi) is effected by rectification. For rectificative removal, it is possible in principle to use any suitable apparatus or any suitable combination of apparatuses. Preference is given here to using at least one column, further preferably one or two columns, further preferably one column, having separating internals in accordance with the invention. Particular preference is given to using a distillation column. Particular preference is given to using one column operated as a rectification column with separating internals; further preference is given to using a column operated as a rectification column and having mass transfer trays as separating internals.

In principle, the at least one column for the removal in (vii) is not restricted in terms of theoretical plates, provided that the described removal in (vii) is achieved. Preferably, the at least one column for the removal in (vii) has 2 to 40, preferably 5 to 30, further preferably 10 to 20, further preferably 14 to 16, theoretical plates.

In principle, the removal in (vii) can be effected at any suitable pressure. Preferably, the removal in (vii) is effected at a pressure at the top of the column in the range from 0.05 to 6 bar, preferably in the range from 0.1 to 4 bar, further preferably in the range from 1 to 2.5 bar.

Equally, the removal in (vii) can in principle be effected at any suitable temperature. Preferably, the separation in (vii) is effected at a temperature in the bottom of the column in the range from 40 to 200° C., preferably in the range from 60 to 160° C., further preferably in the range from 80 to 140° C.

Preferably, the separation in (vii) is conducted at a pressure at the top of the column in the range from 0.05 to 6 bar, preferably in the range from 0.1 to 4 bar, further preferably in the range from 1 to 2.5 bar, and at the same time, for each of the pressure ranges mentioned, at a temperature in the bottom of the column in the range from 40 to 200° C., preferably in the range from 60 to 160° C., further preferably in the range from 80 to 140° C.

In principle, stream S11 can be withdrawn in the stripping section of the column, in the rectifying section of the column or from the top of the column in (vii). Preferably, stream S11 is withdrawn from the top of the column in (vii).

The stream S11 withdrawn from the top of the column in (vii) is not restricted in terms of its further use. For example, it is possible that stream S11 is sent to a process other than that according to the invention. It is preferable to recycle a portion of stream S11 in condensed form into the top of the column in (vii) as reflux. Preferably, a portion of stream S11 is recycled in condensed form into the top of the column in (vii) as reflux, the reflux ratio being unrestricted in principle. Preferably, a portion of stream S11, preferably from 25% to 40% by weight, further preferably from 30% to 35% by weight, of stream S11 is recycled in condensed form into the top of the column as reflux. Further preferably, a portion of stream S11, preferably from 25% to 40% by weight, further preferably from 30% to 35% by weight, of stream S11, optionally after condensation and cooling to a temperature in the range from 95 to 110° C., preferably in the range from 100 to 110° C., is recycled into the top of the column in (vii) as reflux.

In a further preferred embodiment of the process according to the present invention, a portion of stream S11, as already mentioned above, is recycled into a preceding stage of the process, which achieves another increase in the degree of integration of the overall process. Accordingly, it is preferable to effect the separation in (vii) by rectificative means, using at least one column, preferably one or two columns, further preferably one column, equipped with separating internals, preferably mass transfer trays. Further preferably, the separation in (vii) is effected by rectificative means, using at least one column, preferably one or two columns, further preferably one column, equipped with separating internals, preferably mass transfer trays, and with recycling of a portion of the stream S11 produced in (vii), preferably from 60% to 75% by weight, further preferably from 65% to 70% by weight, of stream S11, optionally after condensation and cooling to a temperature in the range from 15 to 40° C., preferably in the range from 20 to 30° C., into the top of one of the columns in (ii), preferably of the column in (ii), as external reflux.

In principle, stream S12 can be withdrawn in the stripping section of the column, in the rectifying section of the column or from the bottom of the column in (vii). Preferably, stream S12 is withdrawn from the bottom of the column in (vii).

The stream S12 withdrawn from the bottom of the column in (vii) is not restricted in principle in terms of its further use. For example, it is possible that stream S12 is used in a process other than that according to the invention. It is preferable to recycle a portion of stream S12, optionally after heating and/or at least partial evaporation, preferably after at least partial evaporation, into the bottom of the column in (vii). Preferably, a portion of stream S12, after at least partial evaporation, is recycled into the bottom of the column in (vii), with no restriction in principle on the evaporation rate used for recycling. Preferably, the evaporation rate used for recycling is in the range from 1% to 40%, further preferably from 2% to 30%, further preferably from 3% to 25%, further preferably from 4% to 20%, further preferably from 5% to 15%.

As described in detail above, the present invention provides a highly integrated process for preparing acrylic acid in which numerous streams and partial streams can be recycled into the process, whether to produce reactant streams, in which case these recycling operations drastically reduce the use of fresh reactants, or as reflux streams into rectification columns used with preference, which increases the separation efficiency. More particularly, it is a feature of the process according to the invention that particular recycling operations involve entirely different process stages, which illustrates that the process according to the invention provides an exceptionally finely adjusted, well-balanced overall process, beginning with the partial oxidation of methanol and ending with the removal of the acrylic acid-comprising product stream, which takes account of all the chemical and energetic specifics of acrylic acid production and configures them advantageously in all aspects.

The present invention is illustrated in detail by the following embodiments and combinations of embodiments which are apparent from the corresponding dependency references and other references:

1. A process for preparing acrylic acid from methanol and acetic acid, comprising
   (i) contacting a gaseous stream S0 comprising methanol, oxygen and inert gas with an oxidation catalyst to obtain a gaseous stream S1 comprising formaldehyde and inert gas;
   (ii) removing at least a portion of the inert gas present in S1 from at least a portion of the formaldehyde present in S1 by absorbing this formaldehyde in an absorbent to obtain a gaseous stream S2 comprising the portion of the inert gas removed, and to obtain a stream S3 comprising absorbent and absorbate comprising formaldehyde;
   (iii) optionally removing a portion or the entirety of the absorbent present in stream S3, such that a stream S3a remains from stream S3, and producing a stream S4 from at least stream S3 or stream S3a and a stream S5 comprising acetic acid; and
   (iv) contacting stream S4 in gaseous form with an aldol condensation catalyst to obtain a gaseous stream S6 comprising acrylic acid.
2. The process according to embodiment 1, wherein from 30% to 100% by weight, preferably from 50% to 98% by weight, further preferably from 70% to 95% by weight, of stream S0 consists of methanol, oxygen and inert gas.
3. The process according to embodiment 1 or 2, wherein, in stream S0, the weight ratio of inert gas to oxygen is in the range from 2.5:1 to 4:1, further preferably in the range from 3:1 to 3.5:1, and at the same time, in each of the two aforementioned cases, the weight ratio of methanol to oxygen is in the range from 2:1 to 3.5:1 or preferably in the range from 2.5:1 to 3:1.
4. The process according to any of embodiments 1 to 3, wherein the inert gas in (i) comprises nitrogen, and preferably at least 95% by weight, further preferably at least 97% by weight, further preferably at least 98% by weight, of the inert gas consists of nitrogen.
5. The process according to any of embodiments 1 to 4, wherein stream S0 additionally comprises water or additionally formaldehyde or additionally water and formaldehyde, preferably additionally water and formaldehyde.
6. The process according to embodiment 5, wherein 1% to 30% by weight, further preferably from 10% to 25% by weight, further preferably from 15% to 25% by weight, of stream S0 consists of water or formaldehyde or water and formaldehyde, preferably water and formaldehyde.
7. The process according to embodiment 6, wherein, in stream S0, the weight ratio of water to oxygen is in the range from 0.5:1 to 2:1, further preferably in the range from 1:1 to 1.5:1, and at the same time, in each of the two aforementioned cases, the weight ratio of formaldehyde to oxygen is in the range from 0.1:1 to 1:1 or preferably in the range from 0.25:1 to 0.75:1.
8. The process according to any of embodiments 1 to 7, wherein the oxidation catalyst in (i) comprises silver, preferably elemental silver, the oxidation catalyst further preferably being an unsupported catalyst comprising 95% by weight or more, further preferably 99% by weight or more, further preferably 99.9% by weight or more, further preferably 99.99% by weight or more, based in each case on the total weight of the unsupported catalyst, of elemental silver.
9. The process according to embodiment 8, wherein the oxidation catalyst in (i) is in the form of granules, the granules preferably having a particle size distribution, determined by means of DIN ISO 3310 from 2010, in the range from 0.1 to 5 mm, further preferably from 0.2 to 4 mm, further preferably from 0.3 to 3 mm, further preferably from 0.5 to 2 mm.

10. The process according to any of embodiments 1 to 9, wherein the contacting in (i) is effected in at least one reactor, preferably at least two reactors, further preferably in at least two reactors connected in parallel, which are preferably operated in alternation (A/B mode).

11. The process according to embodiment 10, wherein the contacting in (i) in the reactor is effected at a catalyst hourly space velocity in the range from 5 to 100 kg/(h*kg), preferably in the range from 15 to 80 kg/(h*kg), further preferably in the range from 25 to 60 kg/(h*kg), the catalyst hourly space velocity being defined as the mass of S0 in kg per hour and per unit mass of catalyst in kg.

12. The process according to embodiment 10 or 11, wherein the contacting in (i) in the reactor is effected at a temperature of the catalyst bed in the range from 500 to 900° C., further preferably in the range from 600 to 800° C., further preferably in the range from 650 to 750° C., and at the same time, for each of the aforementioned temperature ranges, a pressure in the range from 0.5 to 2.5 bar, preferably in the range from 0.8 to 2.2 bar, further preferably in the range from 1 to 2 bar.

13. The process according to any of embodiments 1 to 12, wherein from 55% to 80% by weight, preferably from 60% to 75% by weight, further preferably from 65% to 70% by weight, of stream S1 consists of formaldehyde and inert gas.

14. The process according to any of embodiments 1 to 13, wherein stream S1 additionally comprises water and oxygen, wherein preferably from 15% to 40% by weight, preferably from 20% to 35% by weight, further preferably from 25% to 30% by weight, of stream S1 consists of water and oxygen, and at the same time, for each of the aforementioned cases, the weight ratio of water present in stream S1 to oxygen present in stream S1 is in the range from 25:1 to 50:1, preferably in the range from 35:1 to 45:1.

15. The process according to any of embodiments 1 to 14, wherein stream S1 additionally comprises at least one compound selected from the group consisting of methanol, carbon dioxide, carbon monoxide, hydrogen, methylene glycol and hemiformal, where the total content of these compounds in stream S1 is preferably in the range from 1% to 10% by weight, further preferably in the range from 3% to 9% by weight, further preferably in the range from 5% to 8% by weight.

16. The process according to any of embodiments 1 to 15, additionally comprising
(a) contacting, preferably in countercurrent, a stream S0$a$ comprising oxygen, inert gas and preferably water with a stream S0$b$ comprising methanol to obtain a stream S0$c$ depleted of inert gas and a stream S0 enriched in inert gas, preferably with performance of (a) in a column equipped with separating internals.

17. The process according to embodiment 16, wherein at least 95% by weight, preferably at least 98% by weight, further preferably at least 99% by weight, of stream S0$a$ consists of oxygen, inert gas and preferably water.

18. The process according to embodiment 16 or 17, wherein, in stream S0$a$, the weight ratio of inert gas to oxygen is in the range from 2.5:1 to 4:1, further preferably in the range from 3:1 to 3.5:1, and at the same time, in each of the two aforementioned cases, the weight ratio of water to oxygen is in the range from 0.01:1 to 0.5:1, further preferably in the range from 0.02:1 to 0.1:1.

19. The process according to any of embodiments 16 to 18, wherein at least 95% by weight, preferably at least 98% by weight, further preferably at least 99% by weight, of stream S0$b$ consists of methanol.

20. The process according to any of embodiments 16 to 19, wherein, prior to the contacting of stream S0$a$ with stream S0$b$ in (a), stream S0$a$ is at a temperature in the range from 70 to 100° C., preferably in the range from 75 to 95° C., further preferably in the range from 80 to 90° C., and at the same time, for each of the temperature ranges mentioned, a pressure in the range from 1 to 2 bar, preferably in the range from 1.2 to 1.9 bar, further preferably in the range from 1.4 to 1.8 bar.

21. The process according to any of embodiments 16 to 20, wherein, prior to the contacting of stream S0$a$ with stream S0$b$ in (a), stream S0$b$ is at a temperature in the range from 0 to 100° C., further preferably in the range from 15 to 95° C., further preferably in the range from 20 to 90° C., and at the same time, for each of the temperature ranges mentioned, a pressure in the range from 1 to 2 bar, further preferably in the range from 1.2 to 1.9 bar, further preferably in the range from 1.4 to 1.8 bar.

22. The process according to any of embodiments 16 to 21, wherein at least 95% by weight, preferably at least 98% by weight, further preferably at least 99% by weight, of stream S0$c$ consists of methanol, formaldehyde and preferably water.

23. The process according to any of embodiments 16 to 22, wherein stream S0$c$ has an inert gas content of not more than 1% by weight, preferably not more than 0.1% by weight, further preferably of not more than 0.01% by weight.

24. The process according to any of embodiments 16 to 23, wherein the contacting of S0$a$ and S0$b$ in (a) is effected in countercurrent of S0$a$ relative to S0$b$, preferably using at least one column, further preferably one or two columns, further preferably one column.

25. The process according to embodiment 24, wherein the column has 2 to 20, preferably 3 to 15, further preferably 4 to 10, theoretical plates.

26. The process according to embodiment 24 or 25, wherein S0$a$ and S0$b$ are contacted in (b) at a pressure at the top of the column in the range from 1 to 3 bar, preferably in the range from 1.2 to 2.5 bar, further preferably in the range from 1.5 to 2 bar.

27. The process according to any of embodiments 24 to 26, wherein S0$a$ and S0$b$ are contacted in (b) at a temperature in the bottom of the column in the range from 40 to 80° C., preferably in the range from 45 to 75° C., further preferably in the range from 50 to 70° C.

28. The process according to any of embodiments 24 to 27, wherein stream S0 is withdrawn from the top of the column.

29. The process according to any of embodiments 24 to 28, wherein at least a portion of stream S0$c$ is recycled in liquid form as reflux into the column, preferably into the top of the column.

30. The process according to embodiment 29, wherein at least a portion of stream S0$c$, before being recycled, is heated to a temperature in the range from 80 to 100° C., preferably in the range from 85 to 99° C., further preferably from 90 to 98° C.

31. The process according to any of embodiments 1 to 30, wherein the absorbent in (ii) comprises water or formaldehyde or acetic acid or a mixture of two or three thereof, where preferably at least 80% by weight, further preferably at least 85% by weight, further preferably at least 90% by weight, of the absorbent in (ii) consists of water or of formaldehyde or of acetic acid or a mixture of two or three thereof.
32. The process according to embodiment 31, wherein the absorbent in (ii) comprises water, preferably formaldehyde and water, and further preferably at least 90% by weight, further preferably from 90% to 100% by weight, further preferably from 95% to 100% by weight, of the absorbent in (ii) consists of water and formaldehyde.
33. The process according to embodiment 32, wherein the weight ratio of formaldehyde to water in the absorbent in (ii) is in the range from 0:1 to 2:1, preferably in the range from 0.01:1 to 1:1, further preferably in the range from 0.1:1 to 0.5:1.
34. The process according to any of embodiments 1 to 22, wherein at least 70% by weight, preferably from 75% to 99% by weight, further preferably from 80% to 95% by weight, of stream S2 consists of inert gas.
35. The process according to embodiment 34, wherein stream S2 additionally comprises at least one compound selected from the group consisting of water, methanol, formaldehyde, carbon dioxide, carbon monoxide, oxygen and hydrogen, and optionally at least one compound selected from the group consisting of acetaldehyde, methyl acrylate, methyl acetate, ethene, acetone, methyl formate, methylene glycol, hemiformal and carbon monoxide, where the total content of these compounds in stream S2, based on the total weight thereof, is not more than 30% by weight, preferably in the range from 1% to 25% by weight, further preferably in the range from 5% to 20% by weight.
36. The process according to any of embodiments 1 to 35, wherein at least 80% by weight, preferably to an extent of at least 90% by weight, further preferably to an extent of from 95% to 97% by weight or more consists of water and formaldehyde.
37. The process according to embodiment 36, wherein the weight ratio of water to formaldehyde in stream S3 is in the range from 0.75:1 to 1.25:1, preferably in the range from 0.85:1 to 1.15:1, further preferably in the range from 0.95:1 to 1.05:1.
38. The process according to any of embodiments 1 to 37, wherein the removal in (ii) is effected by absorptive means, preferably using at least one column, further preferably one or two columns, further preferably one column, equipped with separating internals.
39. The process according to embodiment 38, wherein the column in (ii) has 4 to 30, preferably 6 to 20, further preferably 8 to 15, theoretical plates.
40. The process according to embodiment 38 or 39, wherein the removal in (ii) is effected at a pressure at the top of the column in (ii) in the range from 0.5 to 2 bar, preferably in the range from 0.75 to 1.5 bar, further preferably in the range from 0.9 to 1.25 bar.
41. The process according to any of embodiments 38 to 40, wherein the removal in (ii) is effected at a temperature in the bottom of the column in (ii) in the range from 60 to 100° C., preferably in the range from 70 to 90° C., further preferably in the range from 75 to 85° C.
42. The process according to any of embodiments 38 to 41, wherein stream S3 is withdrawn from the bottom of the column in (ii).
43. The process according to embodiment 42, wherein a portion of stream S3, preferably from 75% to 90% by weight, further preferably from 80% to 85% by weight, of stream S3, optionally after cooling to a temperature in the range from 60 to 70° C., preferably in the range from 65 to 70° C., is recycled into the lower part (the lowermost liquid distributor) of the column in (ii) as absorbent.
44. The process according to embodiment 43, wherein the energy required to heat the at least one portion of stream S0c recycled according to embodiment 30 is withdrawn from the bottom of the column in (ii), preferably by means of at least one heat exchanger.
45. The process according to any of embodiments 38 to 44, wherein a liquid stream is withdrawn from at least one lower part of the column in (ii) and recycled into a part higher up, preferably 1 to 3 theoretical plates higher, and preferably at least 90% by weight, further preferably at least 95% by weight, of the stream withdrawn consists of water and formaldehyde.
46. The process according to embodiment 45, wherein the stream withdrawn, before being recycled, is cooled to a temperature in the range from 50 to 60° C., preferably in the range from 55 to 60° C.
47. The process according to any of embodiments 38 to 44, wherein a liquid stream is withdrawn from at least one middle part of the column in (ii) and recycled into a part higher up, preferably 1 to 3 theoretical plates higher, and preferably at least 90% by weight, further preferably at least 93% by weight, of the stream withdrawn consists of water and formaldehyde.
48. The process according to embodiment 47, wherein the liquid stream withdrawn, before being recycled, is cooled to a temperature in the range from 30 to 40° C., preferably in the range from 35 to 40° C.
49. The process according to any of embodiments 38 to 48, comprising
  (a) contacting, preferably in countercurrent, a stream S0a comprising oxygen, inert gas and preferably water with a stream S0b comprising methanol to obtain a stream S0c depleted of inert gas and a stream S0 enriched in inert gas, the contacting in (a) being effected in countercurrent, using one column;
  wherein a stream is withdrawn from at least one upper part of the column in (ii) and at least partly recycled into (a), preferably as external reflux into the column, further preferably into the top of the column.
50. The process according to embodiment 49, wherein at least 90% by weight, preferably from 90% to 98% by weight, further preferably from 92% to 95% by weight, of the stream withdrawn from the at least one upper part of the column in (ii) consists of water and formaldehyde.
51. The process according to any of embodiments 1 to 50, wherein at least 95% by weight, preferably from 95% to 99% by weight, further preferably from 96% to 98% by weight, of stream S4 consists of water, formaldehyde, acetic acid and inert gas.
52. The process according to embodiment 51, wherein stream S4 comprises up to 90% by weight of inert gas, the stream either comprising preferably from 0.1% to 10% by weight, further preferably 0.3% to 5% by weight, further preferably 0.4% to 3% by weight, further preferably 0.5% to 1% by weight, of inert gas, or the stream comprising preferably from 10% to 90% by weight, further preferably from 10% to 85% by weight, further preferably from 20% to 80% by weight, further preferably from 30% to 70% by weight, further preferably from 40% to 60% by weight, of inert gas.
53. The process according to embodiment 51 or 52, wherein the weight ratio of formaldehyde to water in stream S4 is in the range from 0.75:1 to 1.25:1, preferably in the range from 0.85:1 to 1.15:1, further preferably in the range from 0.95:1 to 1.05:1, and at the same time, for each of the aforementioned cases, the weight ratio of acetic acid to water is in the range from 6:1 to 12:1, preferably in the range from 7:1 to 11:1, further preferably in the range from 8:1 to 10:1.

54. The process according to any of embodiments 51 to 53, wherein stream S4 additionally comprises one or more than one compound selected from the group consisting of acrylic acid, methanol, ethene, carbon dioxide and carbon monoxide, where the total content of these compounds in stream S4 is not more than 10% by weight, preferably from 0.1% to 8% by weight, further preferably from 0.5% to 5% by weight.

55. The process according to any of embodiments 1 to 54, wherein stream S5 is produced from a stream S5a comprising acetic acid and a stream S5b comprising acetic acid, at least a portion of stream S5b being a stream recycled from the process beyond (iv).

56. The process according to embodiment 55, wherein at least 90% by weight, preferably at least 95% by weight, further preferably from 95% to 100% by weight, of stream S5a consists of acetic acid.

57. The process according to embodiment 55 to 56, wherein stream S5a additionally comprises at least one compound selected from the group consisting of water, propionic acid and acrylic acid, preferably water and propionic acid, where the total content of these compounds in stream S5a is not more than 10% by weight, preferably not more than 5% by weight, further preferably from 0% to 5% by weight.

58. The process according to any of embodiments 55 to 57, wherein at least 95% by weight, preferably from 95% to 99% by weight, further preferably from 96% to 98% by weight, of the stream S5b recycled from the process consists of acetic acid.

59. The process according to embodiment 58, wherein stream S5b additionally comprises at least one compound selected from the group consisting of water and acrylic acid, preferably water and acrylic acid, where the total content of these compounds in stream S5b is not more than 5% by weight, preferably from 0.5% to 5% by weight, further preferably from 1% to 4% by weight.

60. The process according to any of embodiments 1 to 59, wherein stream S4 is produced in (iii) from stream S3, a stream S5 comprising acetic acid and additionally at least one stream S4a comprising inert gas, carbon dioxide and carbon monoxide, at least a portion of stream S4a being a stream recycled from the process beyond (iv).

61. The process according to embodiment 60, wherein at least 80% by weight, preferably from 80% to 95% by weight, further preferably from 85% to 90% by weight, of the stream S4a recycled from the process consists of inert gas, carbon dioxide and carbon monoxide.

62. The process according to embodiment 61, wherein stream S4a additionally comprises at least one compound selected from the group consisting of water, formaldehyde, acetaldehyde, methanol, methyl acrylate, methyl acetate, ethene, acetone, methyl formate, methylene glycol and hemiformal, where the total content of these compounds in stream S4a is not more than 20% by weight, preferably from 5% to 20% by weight, further preferably from 5% to 10% by weight.

63. The process according to any of embodiments 1 to 62, wherein, in (iii), stream S4 is produced from stream S3, a stream S5 comprising acetic acid, preferably additionally at least one stream S4a comprising inert gas, carbon dioxide and carbon monoxide, and additionally at least one inert gas stream S4b, wherein the inert gas in stream S4b comprises nitrogen, wherein preferably at least 75% by weight, further preferably at least 80% by weight, further preferably at least 90% by weight, of the inert gas in stream S4b consists of nitrogen.

64. The process according to any of embodiments 1 to 63, wherein the aldol condensation catalyst in (iv) comprises a vanadium-phosphorus oxide, preferably having the general empirical formula $V_2O_x(PO_4)_y$, where x is preferably in the range from 1.0 to 2.75, further preferably from 1.5 to 2.25, and y is preferably in the range from 1.5 to 2.5, further preferably from 1.8 to 2.3.

65. The process according to embodiment 64, wherein the aldol condensation catalyst is used in the form of an unsupported catalyst or in supported form on one or more substances preferably selected from the group consisting of $SiO_2$, $TiO_2$, $Al_2O_3$ and $ZrO_2$ or mixtures of two or more thereof, preferably in the form of an unsupported catalyst.

66. The process according to any of embodiments 1 to 65, wherein the contacting in (iv) is effected in at least one reactor, preferably at least two reactors, further preferably in at least two reactors, further preferably in at least two reactors connected in parallel, which are preferably operated in alternation (A/B mode), the reactors preferably being fixed bed reactors.

67. The process according to embodiment 66, wherein the contacting in (iv) in the fixed bed reactor is effected at a catalyst hourly space velocity in the range from 0.01 to 50 kg/(h*kg), preferably in the range from 0.1 to 40 kg/(h*kg), further preferably in the range from 0.5 to 30 kg/(h*kg), the catalyst hourly space velocity being defined as the mass of S4 in kg per hour and per unit mass of aldol condensation catalyst in kg.

68. The process according to embodiment 66 or 67, wherein the contacting in (iv) in the fixed bed reactor is effected at a temperature of the catalyst bed in the range from 200 to 450° C., preferably in the range from 250 to 400° C., further preferably in the range from 290 to 380° C., and at the same time, for each of the aforementioned cases, a pressure in the range from 0.5 to 5 bar, further preferably in the range from 0.8 to 3 bar, further preferably in the range from 1 to 1.8 bar.

69. The process according to any of embodiments 1 to 68, wherein S6 comprises acrylic acid and formaldehyde, preferably acrylic acid, formaldehyde and water, further preferably acrylic acid, formaldehyde, water and acetic acid.

70. The process according to any of embodiments 1 to 69, wherein at least 90% by weight, preferably from 95% to 99% by weight, further preferably from 96% to 98% by weight, of stream S6 consists of acrylic acid, formaldehyde, water, acetic acid and inert gas.

71. The process according to embodiment 70, wherein stream S6 comprises up to 90% by weight of inert gas, the stream either comprising preferably from 0.1% to 10% by weight, further preferably from 0.3% to 5% by weight, further preferably from 0.4% to 3% by weight, further preferably from 0.5% to 1% by weight, of inert gas, or the stream comprising preferably from 10% to 90% by weight, further preferably from 10% to 85% by weight, further preferably from 20% to 80% by weight, further preferably from 30% to 70% by weight, further preferably from 40% to 60% by weight, of inert gas.

72. The process according to embodiment 71, wherein the weight ratio of acrylic acid to water in stream S6 is in the range from 1.0:1 to 2.0:1, preferably in the range from 1.05:1 to 1.75:1, further preferably in the range from 1.1:1 to 1.5:1, at the same time for each of the aforementioned cases the weight ratio of acrylic acid to acetic acid is in the range from 0.1:1 to 0.75:1, preferably in the range from 0.15:1 to 0.5:1, further preferably in the range from 0.2:1 to 0.25:1, and at the same time for each of the aforementioned cases the weight ratio of acrylic acid to formaldehyde is in the range from 4:1 to 9:1, preferably in the range from 5:1 to 8:1, further preferably in the range from 6:1 to 7:1.

73. The process according to embodiment 71 or 72, wherein stream S6 additionally comprises at least one compound selected from the group consisting of acetaldehyde, methanol, methyl acrylate, methyl acetate, ethene, acetone, carbon dioxide and carbon monoxide, where the total content of these compounds in stream S6 is not more than 10% by weight, preferably from 0.1% to 8% by weight, further preferably from 0.5% to 5% by weight.

74. The process according to any of embodiments 1 to 73, wherein the stream S6 obtained in (iv) is at a temperature in the range from 200 to 450° C., preferably in the range from 250 to 400° C., further preferably in the range from 290 to 380° C.

75. The process according to embodiment 74, wherein the stream S6 obtained in (iv) is cooled down to a temperature in the range from 80 to 190° C., preferably in the range from 90 to 180° C., further preferably in the range from 100 to 150° C.

76. The process according to any of embodiments 1 to 74 or according to embodiment 75, wherein stream S6, optionally after cooling, is stored intermediately in a buffer vessel.

77. The process according to any of embodiments 1 to 76, additionally comprising
    (v) removing at least a portion of the formaldehyde present in S6, preferably at least a portion of the formaldehyde and water present in S6, from at least a portion of the acrylic acid present in S6 to obtain an acrylic acid-depleted stream S7 comprising formaldehyde, preferably formaldehyde and water, and to obtain a formaldehyde-depleted, preferably formaldehyde- and water-depleted stream S8 comprising acrylic acid.

78. The process according to embodiment 77, wherein at least 90% by weight, preferably from 90% to 97% by weight, further preferably from 90% to 95% by weight, of stream S7 consists of formaldehyde, water and inert gas.

79. The process according to embodiment 78, wherein stream S7 comprises up to 90% by weight of inert gas, the stream either comprising preferably from 0.1% to 10% by weight, further preferably from 0.3% to 5% by weight, further preferably from 0.4% to 3% by weight, further preferably 0.5% to 1% by weight, of inert gas, or the stream comprising preferably from 10% to 90% by weight, further preferably from 10% to 85% by weight, further preferably from 20% to 80% by weight, further preferably from 30% to 70% by weight, further preferably from 40% to 60% by weight, of inert gas.

80. The process according to embodiment 78 or 79, wherein the weight ratio of formaldehyde to water in stream S7 is in the range from 0.05:1 to 1:1, preferably in the range from 0.05:1 to 0.5:1, further preferably in the range from 0.1:1 to 0.4:1.

81. The process according to any of embodiments 78 to 80, wherein stream S7 additionally comprises at least one compound selected from the group consisting of acrylic acid, acetic acid, acetaldehyde, methanol, methyl acrylate, methyl acetate, ethene, acetone, methyl formate, carbon dioxide and carbon monoxide, where the total content of these compounds in stream S7 is not more than 10% by weight, preferably from 3% to 10% by weight, further preferably from 5% to 10% by weight.

82. The process according to any of embodiments 78 to 81, wherein at least 90% by weight, preferably from 90% to 100% by weight, further preferably from 95% to 100% by weight, of stream S8 consists of acrylic acid and acetic acid.

83. The process according to embodiment 82, wherein the weight ratio of acrylic acid to acetic acid in stream S8 is in the range from 0.05:1 to 1:1, preferably in the range from 0.05:1 to 0.5:1, further preferably in the range from 0.1:1 to 0.3:1.

84. The process according to embodiment 82 or 83, wherein stream S8, in addition to acrylic acid and acetic acid, also comprises water, where the water content of stream S8 is not more than 5% by weight, preferably from 0% to 5% by weight, further preferably from 0% to 2% by weight.

85. The process according to any of embodiments 78 to 84, wherein the removal in (v) is effected by rectificative means, preferably using at least one column, further preferably one or two columns, further one column, equipped with separating internals.

86. The process according to embodiment 85, wherein the column has 30 to 100, preferably 40 to 80, further preferably 50 to 70, theoretical plates.

87. The process according to embodiment 85 or 86, wherein the removal in (v) is effected at a pressure at the top of the column in the range from 0.2 to 2 bar, preferably in the range from 0.5 to 1.5 bar, further preferably in the range from 0.8 to 1.2 bar.

88. The process according to any of embodiments 85 to 87, wherein the removal in (v) is effected at a temperature in the bottom of the column in the range from 90 to 150° C., preferably in the range from 100 to 140° C., further preferably in the range from 110 to 130° C.

89. The process according to any of embodiments 85 to 88, wherein stream S8 is withdrawn from the bottom of the column in (v).

90. The process according to embodiment 89, wherein a portion of stream S8, after being at least partly evaporated, is recycled into the bottom of the column in (v), the evaporation rate used for recycling preferably being in the range from 1% to 40%, further preferably from 2% to 30%, further preferably from 3% to 25%, further preferably from 4% to 20%, further preferably from 5% to 15%.

91. The process according to any of embodiments 77 to 90, wherein stream S8 is sent to a removal stage comprising
    (vi) removing at least a portion of the acrylic acid present in S8 to obtain a stream S9 depleted in acrylic acid compared to S8 and at least one stream S10 enriched in acrylic acid compared to S8.

92. The process according to embodiment 91, wherein at least 95% by weight, preferably from 95% to 99% by weight, further preferably from 96% to 98% by weight, of stream S9 consists of acetic acid and water.

93. The process according to embodiment 92, wherein stream S9 additionally comprises at least acrylic acid, where the total acrylic acid content of stream S9 is not more than 5% by weight, preferably from 1% to 5% by weight, further preferably from 1% to 4% by weight.

94. The process according to any of embodiments 91 to 93, wherein, in (vi), a gaseous stream S10a enriched in acrylic acid and/or acrylic acid adducts and a liquid stream S10b enriched in acrylic acid and/or acrylic acid adducts are obtained.

95. The process according to embodiment 94, wherein at least 90% by weight, preferably from 95% to 99.9% by weight, further preferably from 98% to 99.5% by weight, of the total weight of stream S10a consists of acrylic acid.
96. The process according to embodiment 95, wherein stream S10a additionally comprises acetic acid, where the acetic acid content of stream S10a is not more than 10% by weight, preferably from 0.1% to 5% by weight, further preferably from 0.2% to 2% by weight.
97. The process according to any of embodiments 94 to 96, wherein at least 90% by weight, preferably from 90% to 99.9% by weight, further preferably from 95% to 99.9% by weight, of stream S10b consists of acrylic acid, diacrylic acid and acrylic acid oligomers, preferably of diacrylic acid and acrylic acid oligomers.
98. The process according to embodiment 97, wherein stream S10b additionally comprises acetic acid, where the acetic acid content of stream S10b is not more than 1% by weight, preferably from 0.1% to 1% by weight, further preferably from 0.1% to 0.5% by weight.
99. The process according to any of embodiments 91 to 98, wherein the removal in (vi) is effected by rectificative means, preferably using at least one rectificative column, further preferably one or two rectificative columns, further one rectificative column, equipped with separating internals.
100. The process according to embodiment 99, wherein the rectificative column has 5 to 50, preferably 10 to 40, further preferably 20 to 30, theoretical plates.
101. The process according to embodiment 99 or 100, wherein the removal in (vi) is effected at a pressure at the top of the column in the range from 0.01 to 0.5 bar, preferably in the range from 0.02 to 0.2 bar, further preferably in the range from 0.03 to 0.15 bar.
102. The process according to any of embodiments 99 to 101, wherein the removal in (vi) is effected at a temperature in the bottom of the column in the range from 50 to 120° C., preferably in the range from 60 to 110° C., further preferably in the range from 70 to 100° C.
103. The process according to any of embodiments 99 to 102, wherein stream S10a is withdrawn as a side draw, preferably as a gaseous side draw, from the column in (vi), further preferably as a gaseous side draw in the stripping section of the column.
104. The process according to any of embodiments 99 to 103, wherein a portion of stream S10b, after being at least partly evaporated, is recycled into the bottom of the column in (vi), the evaporation rate used for recycling preferably being in the range from 1% to 40%, further preferably from 2% to 30%, further preferably from 3% to 25%, further preferably from 4% to 20%, further preferably from 5% to 15%.
105. The process according to any of embodiments 99 to 104, wherein stream S9 is withdrawn from the top of the column in (vi).
106. The process according to embodiment 105, wherein a first portion of stream S9, preferably from 55% to 70% by weight, further preferably from 60% to 65% by weight, of the total amount of stream S9, optionally after condensation and cooling to a temperature in the range from 30 to 45° C., preferably in the range from 35 to 40° C., is recycled into the top of the column in (vi) as reflux.
107. The process according to embodiment 106, wherein at least 98% by weight, preferably at least 99% by weight, further preferably at least 99.9% by weight, of the portion of stream S9 recycled into the top of the column in (vi) after condensation and cooling consists of acetic acid, acrylic acid and water, where the acetic acid content is preferably at least 95% by weight, preferably at least 96% by weight, further preferably at least 97% by weight.
108. The process according to any of embodiments 99 to 107, wherein stream S5 is produced from a stream S5a comprising acetic acid and a stream S5b comprising acetic acid, at least a portion of stream S5b being a stream recycled from the process, and a further portion or more than one further portion of stream S9, preferably from 30% to 45% by weight, further preferably from 35% to 40% by weight, of the total amount of stream S9, preferably after condensation and cooling to a temperature in the range from 30 to 45° C., preferably in the range from 35 to 40° C., being recycled into the process as stream S5b.
109. The process according to any of embodiments 77 to 108, wherein, in (iii), stream S4 is produced from stream S3, a stream S5 comprising acetic acid and additionally at least one stream S4a comprising inert gas, carbon dioxide and carbon monoxide, at least one portion of stream S4a being a stream recycled from the process, and a portion of stream S7, a stream S7a, preferably in a first embodiment from 2% to 10% by weight, further preferably from 2% to 8% by weight, of stream S7, based on the total amount thereof, being recycled into the process in uncondensed form as stream S4a, and preferably in a further embodiment from 10% to 90% by weight, further preferably from 30% to 80% by weight, of stream S7, based on the total amount thereof, being recycled into the process in uncondensed form as stream S4a.
110. The process according to embodiment 109, wherein at least 80% by weight, preferably from 80% to 95% by weight, further preferably from 85% to 90% by weight, of stream S7a consists of inert gas, carbon dioxide and carbon monoxide.
111. The process according to embodiment 110, wherein stream S7a additionally comprises at least one compound selected from the group consisting of water, formaldehyde, acetaldehyde, methanol, methyl acrylate, methyl acetate, ethene, acetone, methyl formate, methylene glycol and hemiformal, where the total content of these compounds in stream S7a is not more than 20% by weight, preferably from 5% to 20% by weight, further preferably from 5% to 10% by weight.
112. The process according to any of embodiments 109 to 111, wherein stream S7a is obtained as an uncondensed portion of stream S7 by cooling stream S7 down to a temperature in the range from 30 to 50° C., preferably in the range from 35 to 45° C.
113. The process according to embodiment 112, wherein stream S7a, before being recycled into the process as stream S4a, is heated to a temperature in the range from 150 to 300° C., preferably in the range from 200 to 280° C.
114. The process according to embodiment 112 or 113, wherein stream S7a, before being recycled into the process as stream S4a, is compressed to a pressure in the range from 10.95 to 2 bar, preferably in the range from 1 to 1.5 bar.
115. The process according to any of embodiments 99 to 114, wherein a condensed portion of stream S7, a liquid stream S7b, which is preferably obtained by condensation and cooling to a temperature in the range from 30 to 50° C., further preferably in the range from 35 to 45° C., preferably of 65% to 80% by weight, further preferably of 70% to 75% by weight, of the total amount of stream S7, is recycled into the top of the column in (v) as reflux.

116. The process according to embodiment 115, wherein at least 90% by weight, preferably from 90% to 99% by weight, further preferably from 95% to 98% by weight, of stream S7b consists of formaldehyde and water.

117. The process according to embodiment 116, wherein the weight ratio of formaldehyde to water in stream S7b is in the range from 0.05:1 to 1:1, preferably in the range from 0.05:1 to 0.5:1, further preferably in the range from 0.1:1 to 0.4:1.

118. The process according to embodiment 116 or 117, wherein stream S7b additionally comprises at least one compound selected from the group consisting of acrylic acid, acetic acid, acetaldehyde, methanol, methyl acrylate, methyl acetate, ethene, acetone and methyl formate, where the total content of these compounds in stream S7b is not more than 10% by weight, preferably from 1% to 9% by weight, further preferably from 2% to 5% by weight.

119. The process according to any of embodiments 99 to 118, wherein a portion or more than one portion of stream S7 condensed by cooling stream S7, preferably from 10% to 33% by weight, further preferably from 20% to 26% by weight, of stream S7 is fed as liquid stream 7c to a removal stage comprising
(vii) separating stream S7c into a formaldehyde-enriched stream S11 and a formaldehyde-depleted stream S12.

120. The process according to embodiment 119, wherein at least 90% by weight, preferably from 90% to 98% by weight, further preferably from 90% to 95% by weight, of stream S11 consists of formaldehyde and water.

121. The process according to embodiment 120, wherein the weight ratio of formaldehyde to water in stream S11 is in the range from 0.25:1 to 1:1, preferably in the range from 0.3:1 to 0.8:1, further preferably in the range from 0.35:1 to 0.5:1.

122. The process according to embodiment 120 or 121, wherein stream S11 additionally comprises at least one compound selected from the group consisting of acrylic acid, acetaldehyde, methanol, methyl acrylate, methyl acetate, ethene, acetone and methyl formate, where the total content of these compounds in stream S11 is not more than 10% by weight, preferably from 2% to 10% by weight, further preferably from 5% to 10% by weight.

123. The process according to any of embodiments 119 to 122, wherein at least 98% by weight, preferably from 98% to 99.9% by weight, further preferably from 99% to 99.9% by weight, of stream S12 consists of water and formaldehyde.

124. The process according to embodiment 123, wherein stream S12 additionally comprises at least one of the compounds acrylic acid, acetic acid and methanol, where the total content of these compounds in stream S12 is not more than 2% by weight, preferably from 0.1% to 2% by weight, further preferably from 0.1% to 1% by weight.

125. The process according to any of embodiments 119 to 124, wherein the separation in (vii) is effected by rectificative means, preferably using at least one column, further preferably one or two columns, further preferably one column, equipped with separating internals.

126. The process according to embodiment 125, wherein the column has 2 to 40, preferably 5 to 30, further preferably 10 to 20, theoretical plates.

127. The process according to embodiment 125 or 126, wherein the separation in (vii) is effected at a pressure at the top of the column in the range from 0.05 to 6 bar, preferably in the range from 0.1 to 4 bar, further preferably in the range from 1 to 2.5 bar.

128. The process according to any of embodiments 125 to 127, wherein the separation in (vii) is effected at a temperature in the bottom of the column in the range from 40 to 200° C., preferably in the range from 60 to 160° C., further preferably in the range from 80 to 140° C.

129. The process according to any of embodiments 125 to 128, wherein stream S11 is withdrawn from the top of the column in (vii).

130. The process according to any of the embodiments 125 to 129, wherein a portion of stream S11, preferably from 25% to 40% by weight, further preferably from 30% to 35% by weight, of stream S11, optionally after cooling and condensation to a temperature in the range from 95 to 110° C., preferably in the range from 100 to 110° C., is recycled into the top of the column in (vii) as reflux.

131. The process according to any of embodiments 125 to 130, wherein the separation in (vii) is effected by rectificative means, using at least one column, preferably one or two columns, further preferably one column, equipped with separating internals, and with recycling of a portion of stream S11, preferably from 60% to 75% by weight, further preferably from 65% to 70% by weight, of the total amount of stream S11, optionally after cooling and condensation to a temperature in the range from 15 to 40° C., preferably in the range from 20 to 30° C., into the top of one of the columns in (ii), preferably of the column in (ii), as reflux.

132. The process according to any of embodiments 125 to 131, wherein stream S12 is withdrawn from the bottom of the column in (vii).

133. The process according to embodiment 132, wherein a portion of stream S12, after being at least partly evaporated, is recycled into the bottom of the column in (vii), the evaporation rate used for recycling preferably being in the range from 1% to 40%, further preferably from 2% to 30%, further preferably from 3% to 25%, further preferably from 4% to 20%, further preferably, further preferably from 5% to 15%.

DESCRIPTION OF THE FIGURES

FIG. 1 shows the flow diagram of one configuration of the process according to the invention comprising stages (i), (ii), (iii) and (iv), preferably additionally comprising (v), additionally preferably comprising (vi) or (vii) or (vi) and (vii). The streams S0a, S0b, S0c, S0, S1, S2, S3, S4a, S4b, S4, S5a, S5b, S5, S6, S7a, S7c, S7, S8, S9, S10a, S10b, S11, S12 specified in FIG. 1, and the depicted stages and apparatuses (a), (i), (ii), (iii), (iv), (v), (vi), (vii), are elucidated in detail in the example which follows.

The present invention is illustrated in detail by the examples which follow.

EXAMPLES

Reference Example 1

Calculation of Selectivity

The selectivity of acrylic acid formation based on formaldehyde is calculated according to:

$$S_{AA}^{FA} = \frac{Y_{AA}^{FA}}{X_{FA}}$$

with $$Y_{AA}^{FA} = \frac{(\dot{n}_{AA,out} - \dot{n}_{AA,in})/|\nu_{AA}|}{(\dot{n}_{FA,in})/|\nu_{FA}|} \text{ and } X_{FA} = 1 - \frac{\dot{n}_{FA,out}}{\dot{n}_{FA,in}},$$

where $S_{AA}^{FA}$=selectivity of acrylic acid formation based on formaldehyde
$Y_{AA}^{FA}$=yield of acrylic acid formation based on formaldehyde
$X_{FA}$=conversion of formaldehyde
$\dot{n}_{AA,out}$ molar flow rate of acrylic acid out of the reactor
$\dot{n}_{AA,in}$=molar flow rate of acrylic acid into the reactor
$\nu_{AA}$=stoichiometric factor of acrylic acid
$\dot{n}_{FA,in}$=molar flow rate of formaldehyde into the reactor
$\nu_{FA}$=stoichiometric factor of formaldehyde
$\dot{n}_{FA,out}$=molar flow rate of formaldehyde out of the reactor

Example 1

The example which follows is intended to illustrate the elevated space-time yield of the aldol condensation with relatively low inert gas dilution:
Construction of the Pilot Plant A pilot plant equipped with a feed metering unit and an electrically heated vertical reactor tube was used. The reactor used (stainless steel materials no. 1.4541) had a tube length of 950 mm, an external diameter of 20 mm and an internal diameter of 16 mm. Mounted around the reactor were four copper half-shells (E-Cu F25, external diameter 80 mm, internal diameter 16 mm, length 450 mm). Wound around the half-shells was a heating band, around which was wound insulating tape in turn. The reactor heating temperatures were measured on the outside of the reactor heating shell. In addition, it was possible to measure the temperature within the reactor over the entire catalyst bed with the aid of a thermocouple present in a central sleeve (external diameter 3.17 mm, internal diameter 2.17 mm). At the lower end of the reactor tube, a wire mesh in a so-called catalyst seat prevented the discharge of the catalyst bed. The catalyst seat consisted of a tube of length 5 cm (external diameter 14 cm, internal diameter 10 cm), with the wire mesh (mesh size 1.5 mm) present over the upper opening thereof. Applied to this catalyst seat in the reactor tube were 14 g of a downstream bed of steatite spheres having a diameter of 3-4 mm (bed height 5 cm). The thermocouple was placed onto the center of the downstream bed. Then 105 g in each case of unsupported catalyst of the empirical formula VO(PO)$_4$ were introduced into the reaction tube in undiluted form around the thermocouple in the form of spall of particle size 2.0 to 3.0 mm (bed height 66 cm). Above the catalyst bed were 14 g of an upstream bed of steatite spheres having a diameter of 3-4 mm (bed height 5 cm).

Operation of the Pilot Plant

A solution of trioxane in acetic acid was initially charged in a reservoir vessel under a nitrogen atmosphere. The molar ratio of trioxane, calculated as formaldehyde, to acetic acid was as stated in table 1. A Desaga KP 2000 pump was used to meter in the desired volume flow rate of the solution and convey it into an evaporator coil. The solution was evaporated at 85° C. in the presence of preheated nitrogen. The gas mixture was heated to 180° C. in a preheater and conducted through the reactor which was at a temperature of 310° C. The pressure of the reaction gas was adjusted manually to 1.15 bar+/−0.05 bar. All the gas flows were controlled by means of mass flow meters. Analysis stubs at the reactor inlet and outlet enabled the analysis of the gas composition by online GC measurement. The compositions of the product gas were determined by gas chromatography.

The compositions of the product gas measured after 30 minutes, 4 hours and 10 hours were used to calculate the space-time yield of acrylic acid prepared ($STY_{AA}$) achieved at these times. The space-time yield of acrylic acid prepared is based on the mass of acrylic acid in g which is formed per liter of catalyst per hour. The results are reported in table 1.

TABLE 1

| Experiment number | $n_{acetic\ acid}$ to $n_{formaldehyde}$ mol/mol | $p_{formaldehyde}$ mbar | Reactants/% by volume | | | Space-time yield | | |
|---|---|---|---|---|---|---|---|---|
| | | | acetic acid | formaldehyde | nitrogen | 0.5 h | 4 h | 10 h |
| 1 | 3.0:1 | 52 | 13.7 | 4.5 | 81.8 | 31 | 26 | 21 |
| 2 | 3.0:1 | 105 | 27.4 | 9.1 | 63.5 | 60 | 46 | 34 |
| 3 | 3.0:1 | 158 | 41.0 | 13.7 | 45.3 | 84 | 63 | 45 |
| 4 | 4.4:1 | 53 | 20.3 | 4.6 | 75.1 | 32 | 29 | 26 |
| 5 | 4.4:1 | 106 | 40.8 | 9.2 | 50.0 | 72 | 62 | 44 |
| 6 | 4.4:1 | 159 | 61.2 | 13.8 | 25.0 | 108 | 89 | 70 |

Example 2

The example which follows was run with the aid of the process simulation program CHEMASIM from BASF.
1.1 Saturation Column (b)

Ambient air (S0a) and methanol (S0b) are fed to a saturation column (a) operated in countercurrent. This ambient air is preheated to 90° C., compressed to 1.5 bar and fed in at the bottom of the saturation column (a). The methanol is compressed to 1.5 bar, heated up to boiling point and fed in at the top of the saturation column (a). The liquid withdrawn at the bottom of the saturation column (a), to an extent of 99.9995% by weight and after combination with reflux liquid from the absorption column (ii) with supply of heat and heating up to the boiling point, is fed in at the top of the saturation column. 0.0005% by weight from the bottom stream of the saturation column (a) is discharged as wastewater stream.

The relevant streams S0a, S0b, S0c at the bottom of the saturation column, S0 and the wastewater stream are reported in table 2 together with their compositions.

TABLE 2

| | Stream | | | | |
|---|---|---|---|---|---|
| | S0a | S0b | S0c | S0 | Wastewater |
| State of matter | gas | liquid | liquid | gas | liquid |
| Temperature/° C. | 90.00 | 97.40 | 51.97 | 81.76 | 51.97 |
| Pressure/bar | 1.50 | 1.50 | 1.49 | 1.55 | 1.49 |
| Mass flow rate/kg/h | 1055.16 | 615.70 | 7330.12 | 1996.34 | 0.05 |
| Water concentration/% by wt. | 0.60 | 0.00 | 43.96 | 15.00 | 43.96 |
| Formaldehyde concentration/% by wt. | 0.00 | 0.00 | 21.84 | 5.42 | 21.84 |
| Methanol concentration/% by wt. | 0.00 | 100.00 | 34.19 | 30.27 | 34.19 |
| Oxygen concentration/% by wt. | 23.31 | 0.00 | 0.00 | 11.56 | 0.00 |
| Nitrogen concentration/% by wt. | 76.09 | 0.00 | 0.00 | 37.75 | 0.00 |

The air stream S0a entering the saturation column at the bottom is saturated in the saturation column with the mixture (methanol, water, formaldehyde) in 1.1.

1.2 Contacting in (i)

The methanol in stream S0 is oxidized, to form formaldehyde, with the oxygen in stream S0 in a reactor bed over a silver catalyst, in the present case in the form of silver granules having a particle size distribution of 0.5 to 2 mm, determined to DIN ISO 3310 from 2010. This involved operating two fixed bed reactors of identical design, with flow from the top downward, in A/B mode. The reactions over the catalyst are effected at a temperature in the range from 660 to 700° C. in a gradient with increasing temperature with increasing operating time of the individual reactor, and at a pressure of 1.3 to 1.8 bar in a gradient with increasing pressure with increasing operating time of the individual reactor. After flowing through the catalyst bed, the product is immediately cooled down to about 210° C. in the shell and tube steam generator disposed beneath the catalyst layer. In the shell and tube heat transferer arranged downstream, sprayed with reflux liquid from the bottom of the absorption column (ii), the product gas is cooled further and begins to condense. The mixture (S1) is fed in biphasic form with a 66% by weight gas component and 34% by weight liquid component at 87° C. to the absorption column in (ii). The sprayed shell and tube heat transferers are coupled to the saturator circuit, such that the heat removed via coupling can be used for evaporation in the saturator circuit.

The relevant streams S0 at the reactor inlet and S1 at the reactor outlet are reported in table 3 together with their compositions.

TABLE 3

| | Stream | |
|---|---|---|
| | S0 | S1 |
| State of matter | gas | gas |
| Temperature/° C. | 81.76 | 210.00 |
| Pressure/bar | 1.55 | 1.34 |
| Mass flow rate/kg/h | 1996.34 | 1996.32 |
| Water concentration/% by wt. | 15.00 | 25.87 |

TABLE 3-continued

| | Stream | |
|---|---|---|
| | S0 | S1 |
| Formaldehyde concentration/% by wt. | 5.42 | 29.38 |
| Methanol concentration/% by wt. | 30.27 | 1.19 |

TABLE 3-continued

| | Stream | |
|---|---|---|
| | S0 | S1 |
| Methylene glycol concentration/% by wt. | 0.00 | 0.10 |
| Hemiformal concentration/% by wt. | 0.00 | 0.72 |
| Carbon dioxide concentration/% by wt. | 0.00 | 3.46 |
| Oxygen concentration/% by wt. | 11.56 | 0.62 |
| Carbon monoxide concentration/% by wt. | 0.00 | 0.14% |
| Hydrogen concentration/% by wt. | 0.00 | 0.75 |
| Nitrogen concentration/% by wt. | 37.75 | 37.75% |

1.3 Removal in (ii)

The absorption column in (ii) consists of four stages, each corresponding to 2-3 theoretical plates. In countercurrent with a stream S11 recycled from the process and comprising water and formaldehyde, the formaldehyde is scrubbed out of the gas stream therein, the product being removed from the lowermost stage (S3) in a concentration of 49% by weight. Three stages are executed with random packings and the uppermost stage with Thormann trays. In each stage, the heat of absorption is removed in downstream external heat exchangers, in each case by withdrawing a liquid substream at the lower end of a stage, cooling it in an external heat exchanger and feeding it back to the absorption column (ii) at the upper end of the corresponding stage.

In the lowermost stage, the bottom draw is cooled in a plate heat exchanger, by means of which the heat is removed via coupling into the saturator circuit. The heat exchangers give additional holdup, which provides a longer residence time. The stream (S11) comprising water and formaldehyde supplied scrubs residual formaldehyde and a portion of the methanol out of the highly depleted gas stream in the column in the fourth stage. The liquid stream from the uppermost stage is drawn off virtually completely between stages 3 and 4 and fed to the saturator circuit. A further stream of about half the size is drawn off from the third stage and likewise recycled to the saturation column. The gaseous reactor feed to (i), which has been enriched with water as a result, increases the selectivity and conversion of the reaction to give formaldehyde and reduces coking on the catalyst.

Further recycling streams are implemented in the first and second stages of the absorption column. In the first stage, a stream of about 40 m³/h is drawn off from the bottom and, without cooling, sprayed in the distributor region above the first stage, in order to avoid the deposition of formaldehyde out of the gas phase as paraformaldehyde in solid form on dry and relatively cool surfaces. The tubesheets of the shell and tube heat transferers used for cooling of S1 are likewise sprayed from the front and back with draw streams from stages 1 and 2.

The relevant streams S1 at the reactor outlet, S11 on entry into the top of the absorption column, the recycle stream from (ii) into (a), S3 as transfer stream to (iii) and S2 as offgas stream are reported in table 4 together with their compositions.

TABLE 4

| | Stream | | | | |
|---|---|---|---|---|---|
| | S1 | S11 | Recycle stream into (a) | S3 | S2 |
| State of matter | gas | liquid | liquid | liquid | gas |
| Temperature/° C. | 87 | 25 | 42.98 | 68.39 | 35 |
| Pressure/bar | 1.1 | 1 | 1.12 | 1.03 | 1.07 |
| Mass flow rate/kg/h | 1996.32 | 622.69 | 427.93 | 1273.12 | 917.96 |
| Water conc./% by wt. | 25.87 | 65.91 | 68.59 | 47.27 | 3.51 |
| Acrylic acid conc./% by wt. | 0.00 | 0.01 | 0.01 | 0.00 | 0.00 |
| Formaldehyde conc./% by wt. | 29.38 | 24.75 | 25.27 | 50.00 | 0.47 |
| Acetaldehyde conc./% by wt. | 0.00 | 0.25 | 0.00 | 0.00 | 0.17 |
| Methanol conc./% by wt. | 1.19 | 5.52 | 6.13 | 2.73 | 0.51 |
| Methyl formate conc./% by wt. | 0.00 | 0.02 | 0.00 | 0.00 | 0.01 |
| Methyl acetate conc./% by wt. | 0.00 | 2.85 | 0.00 | 0.00 | 1.94 |
| Methacrylic acid conc./% by wt. | 0.00 | 0.40 | 0.00 | 0.00 | 0.27 |
| Ethene conc./% by wt. | 0.00 | 0.13 | 0.00 | 0.00 | 0.09 |
| Acetone conc./% by wt. | 0.00 | 0.17 | 0.00 | 0.00 | 0.12 |
| Carbon dioxide conc./% by wt. | 3.46 | 0.00 | 0.00 | 0.00 | 7.53 |
| Oxygen conc./% by wt. | 0.62 | 0.00 | 0.00 | 0.00 | 1.35 |
| Carbon monoxide conc./% by wt. | 0.14 | 0.00 | 0.00 | 0.00 | 0.30 |
| Hydrogen conc./% by wt. | 0.75 | 0.00 | 0.00 | 0.00 | 1.64 |
| Nitrogen conc./% by wt. | 37.75 | 0.00 | 0.00 | 0.00 | 82.10 |

1.4 Production of a Stream S4 in (iii)

The formaldehyde stream (S3) obtained in (ii), just like the acetic acid stream S5 (mixture of fresh acetic acid and a recycle stream; S5a and S5b), is fully evaporated in a suitable heat transferer and mixed in gaseous form.

1.5 Contacting of Stream S4 with an Aldol Condensation Catalyst

Subsequently, the stream (S4) obtained in (iii) is contacted in (iv) with an aldol condensation catalyst, in the present case in the form of an unsupported catalyst having a composition of the empirical formula $VO(PO)_4$ which has been shaped into cylindrical extrudates having a cross-sectional area diameter of 3 mm and an average extrudate length of 20 mm. The reaction is conducted at a temperature of 320° C. and a pressure of 1.1 bar in a shell and tube reactor, the catalytically active fixed bed being within the catalyst tubes, around which fluid heat carrier flows. Downstream of the reactor, the gaseous stream (S6) is cooled down to a temperature of about 115° C. by means of a shell and tube apparatus and then fed in gaseous form to the distillation column in (v).

The relevant streams S4 at the reactor inlet and S6 at the reactor outlet are reported in table 5 together with their compositions.

TABLE 5

| | Stream | |
|---|---|---|
| | S4 | S6 |
| State of matter | gas | gas |
| Temperature/° C. | 240.00 | 310.00 |
| Pressure/bar | 1.45 | 1.10 |
| Mass flow rate/kg/h | 7078.40 | 7101.71 |
| Water concentration/% by wt. | 9.02 | 12.81 |
| Acrylic acid concentration/% by wt. | 1.63 | 15.45 |
| Acetic acid concentration/% by wt. | 79.14 | 66.96 |
| Propionic acid concentration/% by wt. | 0.01 | 0.01 |
| Formaldehyde concentration/% by wt. | 8.99 | 2.20 |
| Acetaldehyde concentration/% by wt. | 0.00 | 0.04 |
| Methanol concentration/% by wt. | 0.49 | 0.49 |
| Methyl acetate concentration/% by wt. | 0.01 | 0.40 |

TABLE 5-continued

| | Stream | |
|---|---|---|
| | S4 | S6 |
| Methacrylic acid concentration/% by wt. | 0.00 | 0.06 |
| Ethene concentration/% by wt. | 0.01 | 0.09 |
| Acetone concentration/% by wt. | 0.00 | 0.02 |
| Carbon dioxide concentration/% by wt. | 0.07 | 0.68 |
| Oxygen concentration/% by wt. | 0.00 | 0.00 |
| Carbon monoxide concentration/% by wt. | 0.02 | 0.19 |
| Nitrogen concentration/% by wt. | 0.61 | 0.61 |

1.6 Removal in (v)

The column in (v) is designed as a tray column equipped with a number of crossflow trays equivalent to about 60 theoretical plates, and is operated in rectificative mode. The gaseous feed stream (S6) is fed to about the 15th theoretical plate. A reflux stream (S7b) (not shown in FIG. 1) is applied to the uppermost tray. The vapor from the evaporator which is executed as a shell and tube circulation evaporator and is operated with 4 bar steam is conducted into the column below the first tray. The column in (v) is operated at atmospheric pressure; the bottom temperature is about 130° C. and the top temperature about 100° C. The vapors from the column are partly condensed in a shell and tube apparatus (not shown in FIG. 1), and the liquid component is conducted from there into a distillation column (not shown in FIG. 1) and divided into a reflux stream and a distillate draw stream. The uncondensed component of the vapors (S7a) is recycled into (iii) as cycle gas stream (S4a).

The relevant streams S6 at the column inlet, S7c as condensed distillate stream, S8 as bottom stream and the uncondensed component of the vapors as offgas stream are reported in table 6 together with their compositions.

TABLE 6

| | Stream | | | |
|---|---|---|---|---|
| | S6 | S7c | Offgas | S8 |
| State of matter | gas | liquid | gas | liquid |
| Temperature/° C. | 112.26 | 40 | 200 | 128.01 |
| Pressure/bar | 1.1 | 1.0 | 1.1 | 1.3 |
| Mass flow rate/kg/h | 7101.71 | 1101.35 | 12.96 | 5870.8 |
| Water conc./% by wt. | 12.81 | 80.56 | 3.56 | 0.31 |
| Acrylic acid conc./% by wt. | 15.45 | 0.02 | 0.00 | 18.68 |
| Acetic acid conc./% by wt. | 66.96 | 0.01 | 0.00 | 81.00 |
| Propionic acid conc./% by wt. | 0.01 | 0.00 | 0.00 | 0.01 |
| Formaldehyde conc./% by wt. | 2.20 | 14.14 | 0.30 | 0.00 |
| Acetaldehyde conc./% by wt. | 0.04 | 0.14 | 1.01 | 0.00 |
| Methanol conc./% by wt. | 0.49 | 3.12 | 0.21 | 0.00 |
| Methyl formate conc./% by wt. | 0.00 | 0.01 | 0.12 | 0.00 |
| Methyl acetate conc./% by wt. | 0.40 | 1.62 | 8.03 | 0.00 |
| Methacrylic acid conc./% by wt. | 0.06 | 0.22 | 1.64 | 0.00 |
| Ethene conc./% by wt. | 0.09 | 0.07 | 4.10 | 0.00 |
| Propane conc./% by wt. | 0.00 | 0.00 | 0.11 | 0.00 |
| Acetone conc./% by wt. | 0.02 | 0.10 | 0.19 | 0.00 |
| Methylene glycol conc./% by wt. | 0.00 | 0.00 | 0.02 | 0.00 |

The stream S8 withdrawn from the bottom of the column in (v) is fed to the rectification column in (vi).

1.7 Removal in (vi)

The column in (vi) is designed as a tray column equipped with a number of dual flow trays equivalent to about 25 theoretical plates, and is operated in rectificative mode. The liquid stream S8 is fed to the column as feed to about the 12th theoretical plate. The column is operated under reduced pressure. A top pressure of 50 mbar and a total pressure drop in the column of a further 50 mbar result in a bottom temperature of 80° C. and a top temperature of about 50° C. Above the bottom, the acrylic acid product stream S10a is drawn off in gaseous form and then condensed. High-boiling components such as acrylic acid dimer or oligomers are drawn off in liquid form in the bottom of rectification column (S10b). The acetic acid-rich vapors of the column are condensed virtually completely in a shell and tube apparatus (not shown in FIG. 1), a portion is recycled as liquid reflux to the uppermost tray of the column and the rest is recycled into (iii) as distillate stream. The vapor from the evaporator which is executed as a shell and tube circulation evaporator and is operated with 4 bar steam is conducted into the column below the first tray.

The relevant streams S8 at the column inlet, 9 as condensed distillate stream, S10a crude acrylic acid product stream drawn off in gaseous form and S10b as bottom stream are reported in table 7 together with their compositions.

TABLE 7

| | Stream | | | |
|---|---|---|---|---|
| | S8 | S9 | S10a | S10b |
| State of matter | liquid | liquid | gas | liquid |
| Temperature/° C. | 128.01 | 38.62 | 79.89 | 80 |
| Pressure/bar | 1.3 | 0.08 | 0.1 | 0.1 |
| Mass flow rate/kg/h | 5870.8 | 4860.8 | 1000 | 10 |
| Water conc./% by wt. | 0.31 | 0.37 | 0.00 | 0.00 |

TABLE 7-continued

| | Stream | | | |
|---|---|---|---|---|
| | S8 | S9 | S10a | S10b |
| Acrylic acid conc./% by wt. | 18.68 | 2.00 | 98.96 | 99.72* |
| Acetic acid conc./% by wt. | 81.00 | 97.63 | 1.00 | 0.25 |
| Propionic acid conc./% by wt. | 0.01 | 0.00 | 0.04 | 0.03 |

*may also be present in the form of high-boiling acrylic acid adducts, for example dimer and/or oligomer 1.8 Separation in (vii)

The stream S7 obtained from the column in (v), after removal of stream S7a, is fed to the column in (vii) as stream S7c. The column in (vii) is designed as a column with random packings, equipped with a bed of random packings of a height equivalent to about 15 theoretical plates, and is operated in rectificative mode. The liquid stream S7c is fed to the column as feed to about the 5th theoretical plate via a liquid distributor. The reflux from the condenser fed in above the uppermost bed of random packings via a liquid distributor; the vapor from the evaporator which is executed as a shell and tube circulation evaporator and operated with 4 bar steam is fed in below the lowermost tray. The column in (vii) is operated at a pressure of 2.5 bar, resulting in temperatures of about 120° C. in the top and about 130° C. in the bottom. The vapors are condensed almost completely and divided into reflux and distillate stream (S11). The distillate stream comprising enriched aqueous formaldehyde solution is recycled into the absorption column in (ii) and applied to the uppermost stage therein as already described. The bottom stream S12 of the column in (vii) is fed to a wastewater treatment.

The relevant streams S7c at the column inlet, S11 as condensed distillate stream and S12 as bottom stream are reported in table 8 together with their compositions.

TABLE 8

| | Stream | | |
|---|---|---|---|
| | S7c | S11 | S12 |
| State of matter | liquid | liquid | liquid |
| Temperature/° C. | 40.00 | 102.36 | 120.79 |
| Pressure/bar | 1.00 | 2.00 | 2.05 |
| Mass flow rate/kg/h | 1101.35 | 622.69 | 478.57 |
| Water conc./% by wt. | 80.56 | 65.91 | 99.62 |
| Acrylic acid conc./% by wt. | 0.02 | 0.01 | 0.03 |
| Acetic acid conc./% by wt. | 0.01 | 0.00 | 0.02 |
| Formaldehyde conc./% by wt. | 14.14 | 24.75 | 0.32 |
| Acetaldehyde conc./% by wt. | 0.14 | 0.25 | 0.00 |
| Methanol conc./% by wt. | 3.12 | 5.52 | 0.01 |
| Methyl formate conc./% by wt. | 0.01 | 0.02 | 0.00 |
| Methyl acetate conc./% by wt. | 1.62 | 2.85 | 0.00 |
| Methacrylic acid conc./% by wt. | 0.22 | 0.40 | 0.00 |
| Ethene conc./% by wt. | 0.07 | 0.13 | 0.00 |
| Acetone conc./% by wt. | 0.10 | 0.17 | 0.00 |

U.S. Provisional Patent Application No. 62/031,171, filed 31 Jul. 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

Literature Cited

US 20130085294 A1

The invention claimed is:

1. A process for preparing acrylic acid from methanol and acetic acid, the process comprising
   (i) contacting a gaseous stream S0 comprising methanol, oxygen and inert gas with an oxidation catalyst to obtain a gaseous stream S1 comprising formaldehyde and inert gas;
   (ii) removing at least a portion of the inert gas present in S1 from at least a portion of the formaldehyde present in S1 by absorbing this formaldehyde in an absorbent comprising water and formaldehyde to obtain a gaseous stream S2 comprising the portion of the inert gas removed, and to obtain a stream S3 comprising the absorbent and an absorbate comprising the formaldehyde obtained in (i);
   (iii) optionally removing a portion or an entirety of the absorbent present in the stream S3, such that a stream S3a remains from the stream S3, and producing a stream S4 from at least the stream S3 or the stream S3a and a stream S5 comprising acetic acid; and
   (iv) contacting the stream S4 in gaseous form with an aldol condensation catalyst to obtain a gaseous stream S6 comprising acrylic acid;
   wherein the water of the absorbent comprises water obtained in the aldol condensation (iv) which is recycled to (ii), and
   the formaldehyde of the absorbent comprises unconverted formaldehyde from the aldol condensation (iv) which is recycled to (ii).

2. The process according to claim 1, wherein the oxidation catalyst in (i) comprises silver.

3. The process according to claim 1, further comprising
   (a) contacting a stream S0a comprising oxygen and inert gas with a stream S0b comprising methanol to obtain a stream S0c depleted of inert gas and a stream S0 enriched in inert gas.

4. The process according to claim 3, wherein the contacting of S0a and S0b in (a) is effected in countercurrent of S0a relative to S0b.

5. The process according to claim 1, wherein the removing (ii) is effected by at least one column, equipped with separating internals.

6. The process according to claim 5, wherein the stream S3 is withdrawn from a bottom of the column in (ii).

7. The process according to claim 6, wherein a portion of the stream S3, optionally after cooling to a temperature in a range from 60 to 70° C., is recycled into a lower part of the column in (ii) as absorbent.

8. The process according to claim 5, comprising
   (a) contacting a stream S0a comprising oxygen and inert gas with a stream S0b comprising methanol to obtain a stream S0c depleted of inert gas and a stream S0 enriched in inert gas, the contacting in (a) being effected in countercurrent, using one column;
   wherein a stream is withdrawn from at least one upper part of the column in (ii) and at least partly recycled into (a).

9. The process according to claim 1, wherein at least 95% by weight of the stream S4 consists of water, formaldehyde, acetic acid and inert gas.

10. The process according to claim 1, wherein the stream S4 is produced in (iii) from the stream S3, the stream S5 comprising acetic acid and additionally at least one stream S4a comprising inert gas, carbon dioxide and carbon monoxide, at least a portion of the stream S4a being a stream recycled from the process beyond (iv).

11. The process according to claim 1, wherein the aldol condensation catalyst in (iv) comprises a vanadium-phosphorus oxide.

12. The process according to claim 1, wherein S6 comprises acrylic acid and formaldehyde.

13. The process according to claim 1, further comprising
   (v) removing at least a portion of the formaldehyde present in S6 from at least a portion of the acrylic acid present in S6 to obtain an acrylic acid-depleted stream S7 comprising formaldehyde and to obtain a formaldehyde-depleted stream S8 comprising acrylic acid.

14. The process according to claim 13, wherein the stream S8 is sent to a removal stage comprising
   (vi) removing at least a portion of the acrylic acid present in S8 to obtain a stream S9 depleted in acrylic acid compared to S8 and at least one stream S10 enriched in acrylic acid compared to S8.

15. The process according to claim 14, wherein the removing (vi) is effected by at least one rectificative column, equipped with separating internals.

16. The process according to claim 15, wherein the stream S9 is withdrawn from a bottom of the column in (vi).

17. The process according to claim 16, wherein a first portion of the stream S9, optionally after condensation and cooling to a temperature in a range from 30 to 45° C., is recycled into a top of a column in (ii) as reflux.

18. The process according to claim 14, wherein the stream S5 is produced from a stream S5a comprising acetic acid and a stream S5b comprising acetic acid, at least a portion of the stream S5b being a stream recycled from the process, and a further portion or more than one further portion of the stream S9 being recycled into the process as the stream S5b.

19. The process according to claim 13, wherein the stream S4 is produced in (iii) from the stream S3, the stream S5 comprising acetic acid and additionally at least one stream S4a comprising inert gas, carbon dioxide and carbon monoxide, at least a portion of the stream S4a being a stream recycled from the process, and a portion of the stream S7, a stream S7a, being recycled into the process in uncondensed form as the stream S4a.

20. The process according to claim 19, wherein, as the stream S7a, from 2% to 10% by weight of the stream S7, based on a total amount thereof, is recycled into the process in uncondensed form as the stream S4a or, as the stream S7a, from 10% to 90% by weight of the stream S7, based on the total amount thereof, is recycled into the process in uncondensed form as the stream S4a.

21. The process according to claim 13, wherein a condensed portion of the stream S7, a liquid stream S7b, is recycled into a top of a column in (v) as reflux.

22. The process according to claim 13, wherein a portion or more than one portion of the stream S7 condensed by cooling the stream S7 is fed as a liquid stream 7c to a removal stage comprising
   (vii) separating the stream S7c into a formaldehyde-enriched stream S11 and a formaldehyde-depleted stream S12.

23. The process according to claim 22, wherein the separating (vii) is effected by at least one column, equipped with separating internals.

24. The process according to claim 23, wherein a portion of the stream S11, optionally after cooling and condensation to a temperature in a range from 95 to 110° C., is recycled into a top of the column in (vii) as reflux.

25. The process according to claim 22, wherein the separating (vii) is effected by rectification, comprising at least one column equipped with separating internals, and with recycling of a portion of the stream S11, optionally after cooling and condensation to a temperature in a range from 15 to 40° C., into a top of one of columns in (ii) as reflux.

\* \* \* \* \*